(12) United States Patent
Ahrens

(10) Patent No.: US 8,147,806 B2
(45) Date of Patent: Apr. 3, 2012

(54) CELLULAR LABELING FOR NUCLEAR MAGNETIC RESONANCE TECHNIQUES

(75) Inventor: Eric T. Ahrens, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 869 days.

(21) Appl. No.: 10/586,015

(22) PCT Filed: Jan. 11, 2005

(86) PCT No.: PCT/US2005/000800
§ 371 (c)(1), (2), (4) Date: Aug. 4, 2008

(87) PCT Pub. No.: WO2005/072780
PCT Pub. Date: Aug. 11, 2005

(65) Prior Publication Data
US 2008/0292554 A1    Nov. 27, 2008

Related U.S. Application Data

(60) Provisional application No. 60/537,303, filed on Jan. 16, 2004, provisional application No. 60/621,961, filed on Oct. 25, 2004.

(51) Int. Cl.
*A61B 5/00* (2006.01)
*A61B 5/055* (2006.01)

(52) U.S. Cl. ........... 424/9.6; 424/9.5; 424/9.8; 424/450; 514/450; 514/832; 514/937

(58) Field of Classification Search ............... 424/9, 9.5, 424/9.6, 9.8, 450; 514/450, 832, 937
See application file for complete search history.

(56) References Cited

U.S. PATENT DOCUMENTS

| | | | |
|---|---|---|---|
| 4,094,911 A | 6/1978 | Zollinger et al. | |
| 4,558,279 A | 12/1985 | Ackerman et al. | |
| 4,570,004 A | 2/1986 | Lagow et al. | |
| 4,714,680 A | 12/1987 | Civin | |
| 4,783,401 A | 11/1988 | Horan et al. | |
| 4,838,274 A | 6/1989 | Schweighardt et al. | |
| 4,935,223 A * | 6/1990 | Phillips ..................... | 424/1.17 |
| 4,990,283 A | 2/1991 | Visca et al. | |
| 4,996,041 A | 2/1991 | Arai et al. | |
| 5,061,620 A | 10/1991 | Tsukamoto et al. | |
| 5,114,703 A | 5/1992 | Wolf et al. | |
| 5,196,348 A * | 3/1993 | Schweighardt et al. ...... | 436/173 |
| 5,330,681 A | 7/1994 | Brunetta et al. | |
| 5,397,562 A | 3/1995 | Mason et al. | |
| 5,437,994 A | 8/1995 | Emerson et al. | |
| 5,460,800 A * | 10/1995 | Walters ........................ | 424/9.6 |
| 5,486,359 A | 1/1996 | Caplan et al. | |
| 5,539,059 A | 7/1996 | Bierschenk et al. | |
| 5,589,376 A | 12/1996 | Anderson et al. | |
| 5,643,741 A | 7/1997 | Tsukamoto et al. | |
| 5,690,907 A * | 11/1997 | Lanza et al. ................... | 424/9.5 |
| 5,716,827 A | 2/1998 | Tsukamoto et al. | |
| 5,750,397 A | 5/1998 | Tsukamoto et al. | |
| 5,753,506 A | 5/1998 | Johe | |
| 5,763,197 A | 6/1998 | Tsukamoto et al. | |
| 5,766,948 A | 6/1998 | Gage et al. | |
| 5,785,950 A | 7/1998 | Kaufman et al. | |
| 5,824,489 A | 10/1998 | Anderson et al. | |
| 5,827,735 A | 10/1998 | Young et al. | |
| 5,843,780 A | 12/1998 | Thomson | |
| 5,851,832 A | 12/1998 | Weiss et al. | |
| 5,914,108 A | 6/1999 | Tsukamoto et al. | |
| 5,925,567 A | 7/1999 | Kraus et al. | |
| 5,942,225 A | 8/1999 | Bruder et al. | |
| 5,958,371 A | 9/1999 | Lanza et al. | |
| 5,972,703 A | 10/1999 | Long et al. | |
| 6,040,180 A | 3/2000 | Johe | |
| 6,090,622 A | 7/2000 | Gearhart et al. | |
| 6,171,610 B1 | 1/2001 | Vacanti et al. | |
| 6,190,910 B1 | 2/2001 | Kusakabe et al. | |
| 6,200,806 B1 | 3/2001 | Thomson | |
| 6,245,566 B1 | 6/2001 | Gearhart et al. | |
| 6,331,406 B1 | 12/2001 | Gearhart et al. | |
| 6,361,996 B1 | 3/2002 | Rao et al. | |
| 6,468,794 B1 | 10/2002 | Uchida et al. | |
| 6,511,967 B1 | 1/2003 | Weissleder et al. | |
| 7,357,937 B2 | 4/2008 | Hsu et al. | |
| 7,514,074 B2 | 4/2009 | Pittenger et al. | |
| 2002/0016002 A1 | 2/2002 | Toma et al. | |
| 2002/0045259 A1 | 4/2002 | Lim et al. | |

(Continued)

FOREIGN PATENT DOCUMENTS

DE    2 242 191    4/1972

(Continued)

OTHER PUBLICATIONS

C. Wilhelm et al Magnetophoresis and ferromagnetic resonance of magnetically labeled cells, Eur. Biophys. J. 31, 118-125, 2002.*

(Continued)

*Primary Examiner* — Michael G Hartley
*Assistant Examiner* — Jagadishwar Samala
(74) *Attorney, Agent, or Firm* — Ropes & Gray LLP

(57) ABSTRACT

The disclosure provides, in part, fluorocarbon imaging reagents and formulations for the ex vivo labeling of cells. Labeled cells may be detected in vivo or ex vivo by a nuclear magnetic resonance technique, such as magnetic resonance imaging (MRI) or magnetic resonance spectroscopy (MRS). The disclosure additionally provides methods for using the imaging reagents in a variety of clinical procedures.

22 Claims, 15 Drawing Sheets

U.S. PATENT DOCUMENTS

| | | | |
|---|---|---|---|
| 2002/0068045 | A1 | 6/2002 | Reubinoff et al. |
| 2002/0123143 | A1 | 9/2002 | Toma et al. |
| 2002/0192688 | A1 | 12/2002 | Yang et al. |
| 2003/0003574 | A1 | 1/2003 | Toma et al. |
| 2004/0109824 | A1 | 6/2004 | Hinds et al. |
| 2005/0008572 | A1 | 1/2005 | Prokop et al. |
| 2005/0079131 | A1 | 4/2005 | Lanza et al. |
| 2005/0244384 | A1 | 11/2005 | Law |
| 2006/0040389 | A1 | 2/2006 | Murry et al. |
| 2006/0239919 | A1 | 10/2006 | Wickline et al. |
| 2007/0253910 | A1 | 11/2007 | Ahrens et al. |
| 2007/0258886 | A1 | 11/2007 | Ahrens et al. |
| 2009/0263329 | A1 | 10/2009 | Wickline et al. |

FOREIGN PATENT DOCUMENTS

| | | |
|---|---|---|
| DE | 42 03 254 | 5/1996 |
| EP | 0 307 863 | 7/1991 |
| EP | 0 307 087 | 6/1994 |
| EP | 1 728 788 | 12/2006 |
| WO | WO91/14664 | 10/1991 |
| WO | WO94/18954 | 9/1994 |
| WO | WO-94/21303 | 9/1994 |
| WO | WO96/41647 | 12/1996 |
| WO | WO97/40679 | 11/1997 |
| WO | WO 97/40679 | 11/1997 |
| WO | WO-98/20907 | 5/1998 |
| WO | WO-00/02654 | 1/2000 |
| WO | WO-00/53795 | 9/2000 |
| WO | WO2005/072780 | 8/2005 |
| WO | WO2006/096499 | 9/2006 |
| WO | WO2007/100715 | 9/2007 |
| WO | WO2008/119790 | 10/2008 |
| WO | WO 2008/144028 | 11/2008 |
| WO | WO2009/009105 | 1/2009 |

OTHER PUBLICATIONS

Barnett et al., Radiopaque Alginate Microcapsules for X-ray Visualization and Immunoprotection of Cellular Therapeutics, Mol. Pharm. 3(5):531-538 (2006).

Ahrens and Dubowitz, "Peripheral somatosensory fMRI in mouse at 11.7T," *NMR Biomed.*, 14:318-324 (2001).

Ahrens et al., "Receptor-mediated endocytosis of iron-oxide particles provides efficient labeling of dendritic cells for in vivo MR imaging," *Magnetic Resonance in Medicine*, 49:1006-1013 (2003).

Ahrens et al., "A model for MRI contrast enhancement using $T_1$ agents," Proc. Natl. Acad. Sci. USA, 95:8443-8448.

Dardzinski and Sotak, "Rapid tissue oxygen tension mapping using 19F inversion-recovery echo-planar imaging of perfluoro-15-crown-5-ether," *Magnetic Resonance in Medicine.* 32(1):88-97 (1994).

Derossi et al, "The Third Helix of the Antennapedia Homeodomain Translocates through Biological Membranes," *The Journal of Biological Chemistry*, 269(14):10444-10450 (1994).

Derossi et al., "Cell Internationalization of the Third Helix of the Antennapedia Homeodomain is Receptor-Independent," *The Journal of Biological Chemistry*, 271(30):18188-18193 (1996).

Dodd et al., "Normal T-cell response and in vivo magnetic resonance imaging of T cells loaded with HIV transactivator-peptide-derived superparamagnetic nanoparticles", *Journal of Immunological Methods*, 256(1-2):89-105 (2001).

Dousset et al., "In vivo macrophage activity Imaging in the central nervous system detected by magnetic resonance", *Magnetic Resonance in Medicine*, 41(2): 329-333 (1999).

Duong and Kim, "In vivo MR measurements of regional arterial and venous blood volume fractions in intact rat brain", *Magnetic Resonance in Medicine*, 43(3):393-402 (2000).

Eidelberg et al., "19F NMR imaging of blood oxygenation in the brain", *Magnetic Resonance in Medicine*, 6(3):344-52 (1988).

Feili-Hariri, M. et al., "Immunotherapy of NOD mice with bone marrow-derived dendritic cells",*Diabetes*, 48:2300-2308 (1999).

Fishman et al., "Oxygen-sensitive 19F NMR imaging of the vascular system in vivo", *Magnetic Resonance in Medicine*, 5(4):279-85 (1987).

Forstrom et al., "18F-FDG Labelling of Human Leukocytes," *Nuclear Medicine Communications*, 21(7):691-694 (2000).

Frankel et al.. "Cellular uptake of the tat protein from human immunodeficiency virus," *Cell*, 55:1189-1193 (1989).

Friedrich and Sonano, Promoter traps in embryonic stem cells: a genetic screen to identify and mutate developmental genes in mice, *Genes & Development*, 5:1513-1523 (1991).

Girolomoni et al., "Establishment of a Cell-Line with Features of Early Dendritic Cell Precursors from Fetal Mouse Skin", *European Journal of Immunology*, 25(8):2163-2169 (1995).

Green et al., "Autonomous functional domains of chemically synthesized human immunodeficiency virus tat trans-activator protein," *Cell*, 55:1179-1188 (1988).

Gritti et al.,"Multipotent neural stem cells reside into the rostral extension and olfactory bulb of adult rodents," *The Journal of Neuroscience.*, 22(2):437-445 (2002).

Hoehn et al., "Monitoring of implanted stem cell migration in vivo: A highly resolved in vivo magnetic resonance imaging investigation of experimental stroke in rat",*Proceeding of the National Academy of Sciences of the United States of America*, 99(25):16267-16272 (2002).

Josephson et al., "High-efficiency intracellular magnetic labeling with novel superparamagnetic-tat peptide conjugates", *Bioconjugate Chemistry*, 10(2):186-191 (1999).

Kanno et al., "Macrophage accumulation associated with rat cardiac allograft rejection detected by magnetic resonance imaging with ultrasmall superparamagnetic iron oxide particles", *Circulation*, 104(8):934-938 (2001).

Kimura et al., "Neurite outgrowth of PC12 cells is suppressed by wortmannin, a specific inhibitor of phosphatidylinositol 3-kinase," *The Journal of Biological Chemistry*, 269:18961-18967 (1994).

Krause et al., "Multi-organ, multi-lineage engraftment by a single bone marrow-derived stem cell," *Cell*, 105:369-377 (2001).

Kuppuswamy et al., "Multiple functional domains of Tat, the trans-activator of HIV-1, defined by mutational analysis," *Nucleic Acids Research*, 17:3551-3561 (1989).

Lagasse et al., "Purified hematopoietic stem cells can differentiate into hepatocytes in vivo," *Nature Medicine*, 6(11):1229-1234 (2000).

Lewin et al., "Tat peptide-derivatized magnetic nanoparticles allow in vivo tracking and recovery of progenitor cells", *Nature Biotechnology*, 18(4):410-414 (2000).

Lutz et al., "Measurement of oxygen tensions in the abdominal cavity and in the skeletal muscle using 19F-MRI of neat PFC droplets", *Oxygen Transport to Tissue Xix*, 428:569-572 (1997).

Mason, "Non-invasive physiology: $^{19}$F NMR of perfluorocarbons," *Art. Cells, Blood Subs., and Immob. Biotech.*, 22(4):1141-1153 (1994).

McGoron et al., "Perfluorocarbon Distribution to Liver, Lung and Spleen of Emulsions of Perfluorotributylamine (Ftba) in Pigs and Rats and Perfluorooctyl Bromide (Pfob) in Rats and Dogs by F-19 Nmr-Spectroscopy ", *Artifical Cells Blood Substitutes and Immobilization Biotechnology*, 22(4):1243-1250 (1994).

Means et al., "Chemical modifications of proteins: history and applications," *Bioconjugate Chemistry*, 1:2-12 (1990).

Moore et al., "Uptake of dextran-coated monocrystalline iron oxides in tumor cells and macrophages", *Journal of Magnetic Resonance Imaging*, 7(6):1140-1145 (1997).

Noth et al., "In-Vivo Measurement of Partial Oxygen-Pressure in Large Vessels and in the Reticuloendothelial System Using Fast 19f-Mri", *Magnetic Resonance in Medicine*, 34(5):738-745 (1995).

Noth et al., "Perfluoro-15-crown-5-ether labelled macrophages in adoptive transfer experimental allergic encephalomyelitis", *Artificial Cells Blood Substitutes and Immobilization Biotechnology*, 25(3):243-254 (1997).

Perez et al., "Antennapedia homeobox as a signal for the cellular internalization and nuclear addressing of a small exogenous peptide," *Journal of Cell Science*, 102:717-722 (1992).

Pittenger et al., "Multilineage potential of adult human mesenchymal stem cells," *Science*, 284:143-147 (1999).

Pluchino, S. et al., "Injection of adult neurospheres induces recovery in a chronic model of multiple sclerosis", *Nature*, 422(6933):688-6940 (2003).

Qiu et al., "Null mutation of Dlx-2 results in abnormal morphogenesis of proximal first and second branchial arch derivatives and abnormal differentiation in the forebrain," *Genes & Development*, 9:2523-2538 (1995).

Ruben et al., "Structural and functional characterization of human immunodeficiency virus tat protein," *Journal of Virology*, 63:1-8 (1989).

Sanchez et al., "Highly Concentrated 1,2-bis (perfluoroalkyl) iodoethene emulsion or use as contrast agents for diagnosis," *Journal of Fluorine Chemistry*, 73(2):259-264 (1995).

Schoepf, U. et al., "Intracellular magnetic labeling of lymphocytes for in vivo trafficking studies", *Biotechniques*, 24(4): 24(4):642-6, 648-51 (1998).

Schulze, E. et al., "Cellular uptake and trafficking of a prototypical magnetic iron oxide label in vitro",*Invest Radiol*, 30(10):604-610 (1995).

Weissleder, R. et al., "Magnetically labeled cells can be detected by MR imaging",*Journal of Magnetic Resonance Imaging*, 7(1):258-263 (1997).

Ye et al., "In vivo detection of acute rat renal allograft rejection by MRI with USPIO particles", *Kidney International*, 61(3):1124-1135 (2002).

Yeh, T.C. et al., "In-vivo dynamic mri tracking of rat t-cells labeled with superparamagnetic iron-oxide particles", *Magnetic Resonance in Medicine*, 33:200-208 (1995).

Zhao et al., "Human bone marrow stem cells exhibit neural phenotypes and ameliorate neurological deficits after grafting into the ischemic brain of rats," *Experimental Neurology*, 174:11-20 (2002).

Ablamunits et al., Acceleration of autoimmune diabetes by cyclophosphamide is associated with an enhanced IFN-gamma secretion pathway, J. Autoimmun. 13(4):383-392 (1999).

Ahrens et al., In vivo imaging platform for tracking immunotherapeutic cells, Nat. Biotechnol. 23(8):983-987 (2005).

Allen et al., Cellular delivery of MRI contrast agents, Chem. Bio. 11(3):301-307 (2004).

Anderson et al., Magnetic resonance imaging of labeled T-cells in a mouse model of multiple sclerosis, Ann. Neurol. 55(5):654-659 (2004).

Arbab et al., Efficient magnetic cell labeling with protamine sulfate complexed to ferumoxides for cellular MRI, Blood 15:104(4):1217-23 (2004).

Basse-Lusebrink et al., Multi-color $^{19}$F CSI: Simultaneous detection of differently labeled cells in vivo, Abstract #806, Proc. Int. Soc. Mag. Reson. 17 (2009).

Billotey et al., T-cell homing to the pancreas in autoimmune mouse models of diabetes: in vivo MR imaging, Radiology 236(2):579-587 (2005).

Bulte et al., Preparation of magnetically labeled cells for cell tracking by magnetic resonance imaging. Method Enzymol. 386:275-299 (2004).

Cantor et al., Effector function of diabetogenic CD4 Th1 T cell clones: a central role for TNF-alpha, J. Immunol. 175(11):7738-7745 (2005).

Caruthers et al., In vitro demonstration using 19F magnetic resonance to augment molecular imaging with paramagnetic perfluorocarbon nanoparticles at 1.5 Tesla, Invest. Radiology 41(3):305-312, (2006).

Cheng et al., Characterization of aqueous dispersions of Fe(3)O(4) nanoparticles and their biomedical applications, Biomaterials 26(7):729-738 (2005).

Crowder, et al. "Unique perflourocarbon nanobeacons improve stem/progenitor cell tracking with MRI" FASEB Journal, vol. 20, No. 4, part 1. Mar. 2006, pp. A633, Abstract.

Cunningham et al., Positive contrast magnetic resonance imaging of cells labeled with magnetic nanoparticles, Mag. Res. In Med. 53:999-1005 (2005).

Elster et al., Dyke Award. Europium-DTPA: a gadolinium analogue traceable by fluorescence microscopy, Am. J. Neuroradiol. 10(6):1137-1144 (1989).

Evgenov et al., In vivo imaging of immune rejection in transplanted pancreatic islets, Diabetes 55(9):2419-2428 (2006).

Evgenov et al., In vivo imaging of islet transplantation, Nat. Med. 12(1):144-148 (2006).

Fabien et al., Pancreatic lymph nodes are early targets of T cells during adoptive transfer of diabetes in NOD mice, J. Autoimmun. 8(3):323-334 (1995).

Fan et al., MRI of perfluorocarbon emulsion kinetics in rodent mammary tumours, Phys. Med. & Biol. 51:211-220 (2006).

Flögel et al., In vivo monitoring of inflammation after cardiac and cerebral ischemia by fluorine magnetic resonance imaging, Circulation 118:140-148 (2008).

Floris et al., Blood-brain barrier permeability and monocyte infiltration in experimental allergic encephalomyelitis: a quantitative MRI study, Brain. 127(Pt 3):616-27 (2004).

Granot et al., Labeling fibroblasts with biotin-BSA-GdDTPA-FAM for tracking of tumor-associated stroma by fluorescence and MR imaging, Magn, Reson. Med. 54(4):789-797 (2005).

Gudbjartsson et al., The Rician distribution of noisy MRI data, Magn. Reson. Med. 34(6):910-914 (1995).

Helmer et al. On the correlation between the water diffusion coefficient and oxygen tension in RIF-1 tumors, NMR in Biomedicine, 11(3):120-130 (1998).

Hitchens et al., Comparison of iron-oxide- and perfluorocarbon-based cellular contrast agents for detecting immune cell infiltration in models of organ transplant rejection, Abstract #931, Proc. Int. Soc. Mag. Reson. 17 (2009).

Janjic et al., Self-delivering nanoemulsions for dual fluorine-19 MRI and fluorescence detection, J. Amer. Chem. Soc. 130:2832-2841 (2008).

Jiang et al., The Design and Synthesis of Highly Branched and Spherically Symmetric Fluorinated Oils and Amphiles, Tetrahedron 63(19):3982-3988 (2007).

Kim et al., Interplay of tumor vascular oxygenation and tumor pO2served using near-infrared spectroscopy, an oxygen needle electrode, and 19F MR pO2 mapping, J. Biomed Opt 8:53-62; (2003).

Kircher et al., In vivo high resolution three-dimensional imaging of antigen-specific cytotoxic T-lymphocyte trafficking to tumors, Cancer Res. 63(20):6838-6846 (2003).

Klug et al., 1H/19F molecular MR-imaging in mouse models of acute and chronic inflammation, Abstract #3172, Proc. Int. Soc. Mag. Reson. 17 (2009).

Kraitchman et al., In vivo magnetic resonance imaging of mesenchymal stem cells in myocardial infarction, Circulation 107(18):2290-2293 (2003).

Kravtzoff et al., GD-DOTA Loaded into red blood cells. A new magnetic resonance imaging contrast agents for vascular system, Adv. in Exp. Med. and Biol. 326:347-326 (1992).

Lanza et al., 1H/19F magnetic resonance molecular imaging with perfluorocarbon nanoparticles. In: Ahrens ET, editor. In vivo cellular and molecular imaging, Curr. Top. Dev. Biol. 70:58-78 (2005).

Lanza et al., A novel site-targeted ultrasonic contrast agent with broad biomedical application, Circulation 94(12):3334-3340 (1996).

Laukemper-Ostendorf et al., 19F-MRI of perflubron for measurement of oxygen partial pressure in porcine lungs during partial liquid ventilation, Magn. Reson. Med. 47:82-89; (2002).

Leiter et al., The nonobese diabetic (NOD) mouse, Am. J. Pathol. 128(2):380-383 (1987).

Mason et al., Hexafluorobenzene: a sensitive 19F NMR indicator of tumor oxygenation, NMR Biomed 9:125-134; (1996).

McNAB et al., Tissue oxygen tension measurements in Shionogi model of prostate cancer using $^{19}$F MRS and MRI, MAGMA 17:288-295 (2004).

Meyer et al., Measurement of vascular volume in experimental rat tumors by 19F magnetic resonance imaging, Invest. Radiol. 28(8):710-719 (1993).

Miller et al., Imaging the single cell dynamic of CD4+ T cell activation by dendritic cells in lymph nodes, J. Exp. Med. 200(7):847-856 (2004).

Miyazaki et al., Predominance of lymphocytes-T in pancreatic-islets and spleen of pre-diabetic non-obese diabetic (NOD) mice—a longitudinal-study, Clin. Exp. Immunol. 60(3):622-630 (1985).

Modo et al., Mapping transplanted stem cell migration after a stroke: a serial, in vivo magnetic resonance imaging study, Neuroimage 21(1):311-317 (2004).

Moore et al., Tracking the recruitment of diabetogenic CD8+ T-cells to the pancreas in real time, Diabetes 53(6):1459-1466 (2004).

Morawski et al., Quantitative magnetic resonance immunohistochemistry with ligand-targeted F-19 nanoparticles, Magn. Reson. Med. 52(6):1255-1262 (2004).

Morawski et al., Targeted Nanoparticles for Quantitative Imaging of Sparse Molecular Epitopes with MRK, Mag. Res. in Med. 51(3):480-486 (2004).

Neubauer et al., Endothelial stem cell detection in vivo with unique perflourocarbon nanoparticle labels using fluorine (F-19) MNRI at 1.5 T, Circulation 114(18)(Suppl. S):251 (Abstract) (2006).

Pakala et al., T helper 2 (Th2) T cells induce acute pancreatitis and diabetes in immune-compromised nonobese diabetic (NOD) mice, J. Exp. Med. 186(2):299-306 (1997).

Partlow et al., 19F magnetic resonance imaging for stem/progenitor cell tracking with multiple unique perfluorocarbon nanobeacons, FASEB J. 21:1647-1654 (2007).

Pelchen-Matthews et al., Phorbol ester-induced downregulation of CD4 is a multistep process involving dissociation from p56Ick, increased association with clathrin-coated pits, and altered endosomal sorting, J. Exp. Med. 178(4):1209-1222 (1993).

Phillips et al., MAdCAM-1 is needed for diabetes development mediated by the T cell clone, BDC-2.5, Immunology 116(4):525-531 (2005).

Phillips et al., Nondepleting anti-CD4 has an immediate action on diabetogenic effector cells, halting their destruction of pancreatic beta cells, J. Immunol. 165(4):1949-1955 (2000).

Piacenti et al., Synthesis and characterization of fluorinated polyetheric amides, J. Fluor. Chem. 68:227-235 (1994).

Pintaske et al., A preparation technique for quantitative investigation of SPIO-containing solutions and SPIO-labelled cells by MRI, Biomed. Tech. 50(6):174-180 (2005) (English Abstract).

Ribeiro et al., In vivo dynamics of T cell activation, proliferation, and death in HIV-1 infection: why are CD4+ but not CD8+ T cells depleted? Proc. Natl. Acad. Sci. USA 99(24):15572-15577(2002).

Schneider et al., In vivo microscopic evaluation of the microvascular behavior of FITC-labeled macromolecular MR contrast agents in the hamster skinfold chamber, Invest. Radiol. 35(9):564-570 (2000).

Shapiro et al., In vivo detection of single cells by MRI, Magn. Reson. Med. 55(2):242-249 (2006).

Soloski, Synthesis of perfluoro (polyether) difunctional compounds, J. Fluor. Chem. 11:601-612 (1978).

Sotak et al., A new perfluorocarbon for use on fluorine-19 magnetic resonance imaging and spectroscopy, Magn. Reson. Med. 29:188 (1993).

Srinivas et al., Fluorine-19 MRI for visualization and quantification of cell migration in a diabetes model, Mag. Res. In Med. 58(4):725-734 (2007).

Taylor and Deutsch, 19F-nuclear magnetic resonance: measurements of [O2] and pH in biological systems, Biophys J. 53: 227-233 (1988).

Tonelli et al., Linear perfluoropolyether difunctional oligomers: chemistry, properties and applications, J. Fluorine Chem. 95:51-70 (1999).

Tonelli et al., Perfluoropolyether alkyl diesters: Structure effects of the alkyl group on the kinetics of the hydrolysis reactions, J. Polym. Sci. Part A: Polym Chem. 40:4266-4280 (2002).

Tonelli et al., Perfluoropolyether functional oligomers: unusual reactivity in organic chemistry, J. Fluor. Chem. 118(1-2):107-121 (2002).

Turvey et al., Noninvasive imaging of pancreatic inflammation and its reversal in type 1 diabetes, J. Clin. Invest. 115(9):2454-2461 (2005).

Venanzi et al., Structural properties and photophysical behavior of conformationally constrained hexapeptides functionalized with a new fluorescent analog of tryptophan and a nitroxide radical quencher, Biopolymers 75(2):128-139 (2004).

Wilson et al., Measurement of preretinal oxygen-tension in the vitrectomized human eye using F-19 magnetic resonance spectroscopy, Arch. Ophthalmol-Chic. 110(8):1098-1100 (1992).

Wisner et al., A modular lymphographic magnetic resonance imaging contrast agent: contrast enhancement with DNA transfection potential, J. Med. Chem. 40(25):3992-3996 (1997).

WU et al., In situ labeling of immune cells with iron oxide particles: An approach to detect organ rejection by cellular MRI, Proc. Natl. Acad. Sci. USA 103(6):1852-1857 (2006).

Xia et al., Tumour oxygen dynamics measured simultaneously by near-infrared spectroscopy and F-19 magnetic resonance imaging in rats, Phys. Med. Biol. 51(1):45-60 (2006).

Yeh et al., Intracellular labeling of T-cells with superparamagnetic contrast agents, Magn. Reson. Med. 30(5):617-625 (1993).

You et al., Detection and characterization of T cells specific for BDC2.5 T cell-stimulating peptides, J. Immunol. 170(8):4011-4020 (2003).

Yu et al., High-resolution MRI characterization of human thrombus using a novel fibrin-targeted paramagnetic nanoparticle contrast agent, Mag. Res. In Med. 44:867-872 (2000).

Zhang et al., Synthetic applications of fluorous solid-phase extraction (F-SPE), Tetrahedron 62:11837-11865 (2006).

* cited by examiner

A.

B.

Rxn 1: PFPE-ester + O-aminoethyl-O'-methyl-PEG 750 → PEG2-PFPE

Rxn 2: PFPE-ester + hexadexylamine → bis-hexadecylamido-PFPE

Rxn 3: PFPE-ester + dimyristoyl phosphatidyl ethanolamine → diPE-PFPE

Rxn 4a: PFPE-ester + 1,6-diaminohexane → bis-aminohexyl-PFPE-amide

Rxn 4b: bis-aminohexyl-PFPE-amide + Cy5-NHS ester → di-Cy5-PFPE

CELLULAR LABELING FOR NUCLEAR MAGNETIC RESONANCE TECHNIQUES

RELATED APPLICATIONS

This application is a national stage filing under 35 U.S.C. 371 of International Application PCT/US2005/000800, filed Jan. 11, 2005, which claims the benefit of U.S. Applications No. 60/537,303 filed Jan. 16, 2004 and, Ser. No. 60/621,961, filed Oct. 25, 2004, the specifications of which are incorporated by reference herein. International Application PCT/US2005/000800 was published under PCT Article 21(2) in English.

BACKGROUND

Many biological processes are carried out by dynamic, mobile populations of cells. For example, cells of the immune system are recruited from the bloodstream to areas of inflammation or infection, resulting in an accumulation of immune cells at the affected site. A marked infiltration of immune cells often occurs in tissues affected by autoimmune diseases, cancers and infections. Likewise, transplant rejection is mediated by host immune cells that enter and destroy the transplanted tissue. There is also growing evidence that stem cells originating in the bone marrow migrate through the bloodstream and assist in the regeneration of damaged tissues.

Although dynamic cell populations play a key role in significant diseases, present technologies for monitoring the movement of cells in vivo are quite limited. Typically, cell movements are monitored only in "snap shots" obtained by histological analysis of tissue biopsies. However, the process of sampling a tissue often alters the behavior of cells, and only a limited number of biopsies can be obtained from a particular tissue or organ. Some progress has been made studying cell movements via in vitro assays and isolated tissues ex-vivo. Existing instruments for non-invasive analysis of living organisms are, at present, ill-suited for tracking living cells. Light-based imaging technologies, such as bioluminescence (e.g. luciferases) technologies, are often ineffective at visualizing deep structures because most mammalian tissues are optically opaque. Positron emission tomography (PET) techniques using radioactively-labeled probes are highly sensitive. However, PET instrumentation is often limited to a resolution of several millimeters and is unable to resolve fine details of tissues and organs. Furthermore, labeled cells cannot be detected for time periods that extend beyond a typical PET radioisotope half-life, and generally PET is not useful for longitudinal studies. In order to gain a fundamental understanding of cellular processes, new ways to visualize the population dynamics of specific cell types in vivo must be developed.

Magnetic resonance imaging (MRI) is a widely used clinical diagnostic tool because it is non-invasive, allows views into optically opaque subjects, and provides contrast among soft tissues at reasonably high spatial resolution. Conventional MRI focuses almost exclusively on visualizing anatomy and has no specificity for any particular cell type. The 'probe' used by conventional MRI is the ubiquitous proton ($^1$H) in mobile water molecules. New classes of exogenous MRI probes or reagents are needed to facilitate cell-specific imaging in living subjects.

SUMMARY

In certain aspects, the disclosure provides novel methods and reagents for labeling cells ex vivo with an imaging reagent, such as a fluorocarbon imaging reagent, that can be detected by a nuclear magnetic resonance technique. Labeled cells may be administered to a subject and subsequently detected by nuclear magnetic resonance techniques. Examples of nuclear magnetic resonance techniques include magnetic resonance imaging (MRI) and localized magnetic resonance spectroscopy (MRS). Because nuclear magnetic resonance techniques are generally performed as non-invasive procedures, the labeled cells may be detected at one or more time points in a living subject. Labeled cells may also be detected in a cell culture or in essentially any other milieu on which a nuclear magnetic resonance technique can be performed, such as tissue explants, organs and tissues removed from a subject (possibly prior to transplant into a transplant recipient), artificially generated tissues and various matrices and structures seeded with cells.

In certain aspects, the disclosure provides methods for labeling a cell. Such methods may include contacting the cell ex vivo with a fluorocarbon imaging reagent under conditions such that the fluorocarbon imaging reagent becomes associated with the cell. Perfluoropolyethers (PFPEs) are examples of suitable fluorocarbon imaging reagents. Perfluoropolyethers may be linear or cyclic (e.g., perfluoro-crown ethers). Optionally, the cell may be contacted with the fluorocarbon imaging reagent in the presence of a reagent that enhances uptake of the fluorocarbon imaging reagent. Cationic lipids are an example of a suitable uptake enhancing reagent; other such reagents are described herein and are, in view of this specification, known in the art. While a fluorocarbon imaging reagent may be internalized by a cell, it may also associate with the extracellular surface of a cell. Association with an extracellular surface may be increased by conjugating the imaging reagent to a cellular targeting moiety. A cellular targeting moiety may be essentially any molecular entity that binds to the desired cells, such as an antibody that binds to an epitope that is exposed to the extracellular milieu. Uptake of an imaging reagent into a cell may be increased by conjugating the imaging reagent to an internalization moiety. An internalization moiety is any molecular entity that stimulates or promotes entry of the imaging reagent into the cell. Examples include internalizing peptides and moieties that bind to receptors or other cell surface proteins that are internalized by, for example, receptor mediated endocytosis. An imaging reagent may be formulated as an emulsion. The cell may be essentially any cell, including prokaryotic and eukaryotic cells. In preferred embodiments, the cell is a mammalian cell. In certain embodiments the cell is a cell of the immune system, such as a dendritic cell. A cell may also be a stem cell or a cell that has been prepared for administration to a subject as part of a cellular therapy or a transplant, such as a peripheral blood stem cell transplant or bone marrow transplant.

In certain aspects, the disclosure provides fluorocarbon imaging reagents. Preferred fluorocarbon imaging reagents have one or more of the following properties: tolerable cytotoxicity; a $^{19}$F NMR spectrum that is simple, ideally having a single, narrow resonance to minimize chemical shift artifacts; a large number of NMR-equivalent fluorine atoms per molecule; and suitability for formulation to permit efficient labeling of many cell types. Preferred fluorocarbon imaging reagents include, linear or cyclic perfluoroethers (e.g., perfluoro-crown ethers). Preferred perfluoro-crown ethers include perfluoro-15-crown-5, perfluoro-18-crown-6 and perfluoro-12-crown-4. In certain embodiments, the fluorocarbon imaging reagent is a perfluorinated polyether having an average formula:

wherein Y is selected from the group consisting of:

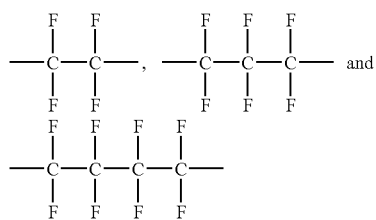

wherein n is an integer from 8 to 20; wherein X and Z are the same and are selected from the group consisting of perfluoroalkyls, perfluoroethers, fluoroalkyls terminated with fluoroacyl, carboxyl, amide or ester, methylols, acid chlorides, amides, amidines, acrylates and esters. In a particularly preferred embodiment, n is 10-12, most preferably 11. In a further embodiment, X and/or Z are polyethers that are terminated with a group (e.g. a carboxyl group) that facilitates the addition of further moieties. Optionally, the imaging reagent comprises an additional functional moiety. The additional functional moiety may be a detection moiety that facilitates detection of the reagent by a technique other than a nuclear magnetic resonance technique. Examples of detection moieties include fluorescent detection moieties and PET detection moieties. Accordingly, the disclosure provides linear fluorocarbons derivatized at one or more polymer ends with at least one functional moiety, wherein the at least one functional moiety is selected from the group consisting of: a detection moiety, a hydrophilic moiety, a targeting moiety and a cellular uptake moiety. The incorporation of a detection moiety creates a dual (or higher order) labeling moiety that facilitates detection by more than one technique (e.g., PET and MRI or fluorescence microscopy and MRS). Optionally, an imaging reagent may be formulated as an emulsion. Preferred emulsions will be stable at body temperature (37° C. for humans) and at a storage temperature, such as 4° C. or room temperature (20-25° C.). Preferably an emulsion is designed to facilitate uptake of the imaging reagent by the subject cells. An emulsion may have an average particle size of between 10 and 500 nm in diameter (meaning that the emulsion may contain particles smaller than 10 nm in diameter or larger than 500 nm in diameter, but having an arithmetical mean particle diameter falling between 10 and 500 nm, as calculated by methods known in the art). Preferably the average particle diameter of the emulsion will be between 30 and 300 nm or between 30 and 200 nm. In certain aspects, the invention provides methods for detecting a cell in a subject. A method may comprise: administering to the subject a cell that is labeled with a fluorocarbon imaging reagent and examining at least a portion of the subject by a nuclear magnetic resonance technique. Such analysis may include MRI or MRS, which may include collecting data for and generating an image of $^{19}F$ distribution. Imaging may also include collecting data for and generating a conventional anatomical $^{1}H$ image. In a preferred embodiment, $^{19}F$ and $^{1}H$ images are generated and compared, optionally by superposition or overlay. Optionally, labeled cells may be detected using $^{19}F$ MRS. In a preferred embodiment a conventional anatomical $^{1}H$ image is used as a template to guide the positions of one or more localized voxels for $^{19}F$ MRS.

In some aspects, the invention provides labeled cellular formulations. A labeled cellular formulation for administration to a subject may comprise a cell; and a fluorocarbon imaging reagent that is associated with the cell, and optionally a pharmaceutically acceptable excipient.

As will be apparent from this disclosure, methods described herein will be useful in a variety of clinical procedures. For example, the disclosure provides methods for detecting donor cells in a recipient, such as a transplant recipient or a recipient of other types of cell-based therapy. Such a method may comprise administering cells for transplant to a transplant recipient, at least a portion of which cells for transplant are labeled with a fluorocarbon imaging reagent; and examining at least a portion of the subject by a nuclear magnetic resonance technique, thereby detecting the labeled cells. Detection of the labeled cells may be done once or repeatedly and may be performed so as to provide information about the location and trafficking of labeled cells in the transplant recipient. Examples of cell recipients include recipients of bone marrow transplants (or cellular fractions containing hematopoietic stem cells, commonly but not exclusively derived from bone marrow, peripheral blood or cord blood) and other cell or organ transplant recipients. Organ transplant recipients include recipients of donor organs such as liver, heart, lung, kidney, pancreatic tissue, neural tissue or other transplants. Recipients also include recipients of donor cells, which may be derived directly from a donor (in the case of autologous cells, the "donor" is the same individual as the recipient) or subjected to limited or extensive culturing prior to use. Donor cells may be derived from essentially any tissue that serves as a source of useful cells, and may include stem cells (including precursor cells), such as hematopoietic stem cells, hemangioblasts, hepatic stem cells, neural stem cells, muscle stem cells (e.g. satellite cells), cardiomyocyte precursor cells, pancreatic stem cells, vascular endothelial precursor cells, mesenchymal stem cells, bone or cartilage precursor cells, or may include mature cells, such as dendritic cells, immune cells (e.g., T cells, B cells), chondrocytes, osteoblasts, and the like. Cells for administration may be autologous, heterologous or even derived from another organism, such as a pig. Other aspects of the present invention will be apparent from the disclosure below.

DETAILED DESCRIPTION

1. Overview

Figure 1:
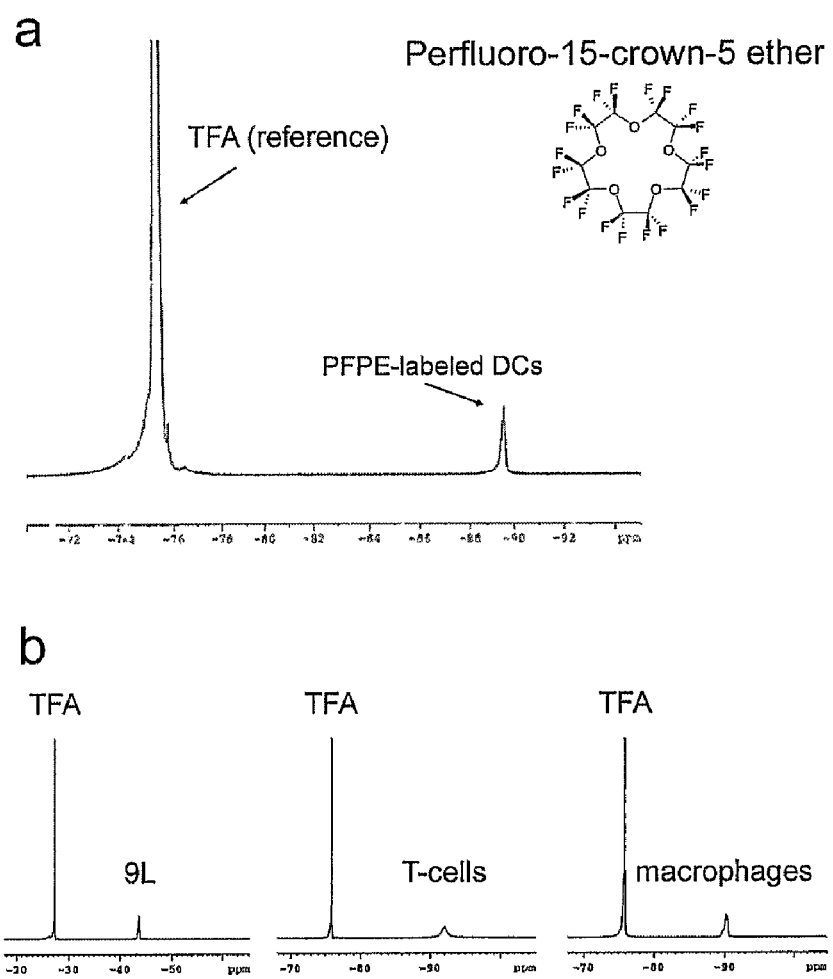
FIG. 1. $^{19}F$ NMR confirms PFPE labeling in a variety of cell types Panel (a) shows a $^{19}F$ NMR spectrum at 282 MHz of PFPE labeled DCs (right peak). Also shown is a reference compound, trifluoroacetic acid (left). The PFPE compound, comprised of perfluoro-15-crown-5 ether, is shown on the upper-right. Panel (b) shows $^{19}F$ NMR spectra for rat 9 L gliosarcoma cells, T-cells, and macrophages labeled with PFPE. Thus many different cells types can readily be labeled with PFPE with comparable efficiency. Data in (b) were measured using similar labeling and measurement procedures as (a).

In certain aspects, the invention provides novel methods and reagents for labeling cells ex vivo with a nuclear magnetic resonance imaging reagent, such as a fluorocarbon imaging reagent. Labeled cells may then be detected by a $^{19}$F nuclear magnetic resonance technique (e.g., MRI/MRS). $^{19}$F nuclear magnetic resonance techniques are excellent imaging tools for biological systems because of the absence of endogenous background signals. Fluorine is present, if at all, at exceedingly low levels in living organisms, and generally not in a chemical form that is detectable by liquid-state nuclear magnetic resonance techniques. This is quite distinct from conventional $^1$H MRI which, while providing visualization of fine anatomical detail, does not permit selective detection of particular cell populations. Certain methods disclosed herein permit whole or partial body screening to visualize the distribution of labeled cells in a living subject. The precise anatomical location of labeled cells detected by $^{19}$F nuclear magnetic resonance may be determined by, for example, superimposition of a $^1$H MRI image that provides anatomical detail. In preferred embodiments, the $^1$H image is acquired during the same imaging session as the $^{19}$F image (without moving the subject) to ensure registration. Additionally, the nuclear magnetic resonance techniques disclosed herein may be applied effectively in ex vivo contexts, as in the case of tissue samples, excised organs and cell cultures. The imaging technology disclosed herein may be applied to a large number of biological and medical problems.

It certain aspects, a method of the invention may comprise labeling cells ex vivo with a $^{19}$F imaging reagent, administering the labeled cells to a subject, and detecting labeled cells in the subject. The cells to be labeled may be a crude cellular fraction or tissue sample, or the cells may be cultured and/or subjected to enrichment prior to labeling. For example, particular cell types may be selected by fluorescence activated cell sorting (FACS) prior to labeling. Other sorting or selective enrichment methods are known in the art for the various different cell types that may be of interest. The types of cells that are labeled may also be controlled by the nature of the imaging reagent. For example, simple colloidal suspensions of imaging reagent will tend to be taken up more quickly by cells with phagocytic activity. As another example, an imaging reagent may be formulated with or covalently bound to a targeting moiety that facilitates selective targeting of the imaging reagent to a particular population of cells. Imaging reagents are described further below. After labeling, cells may be immediately administered or the cells may be stored, further cultured, purified, enriched, segregated or processed in any way that is not incompatible with the intended use of such cells.

In certain aspects, labeled cells will be administered for a therapeutic purpose. Technology described herein may be used for monitoring the trafficking of cellular therapeutics in vivo or in any other desired milieu, such as a tissue explant. Bone marrow cell transplants have been widely used for many years in recipients of ablative therapies for cancers. Various purified cell populations have also been used in place of bone marrow, such as cell populations enriched for hematopoietic stem cells; for example cells may be harvested from umbilical cord blood or peripheral blood. After entering the bloodstream, the stem cells generally travel to the bone marrow, where they begin to produce new white blood cells, red blood cells, and platelets. This engraftment usually occurs within about 2 to 4 weeks after transplantation. Traditionally, engraftment is monitored by testing blood counts on a frequent basis, and complete recovery of immune function generally requires several months (for autologous transplant recipients) to years (for patients receiving allogeneic or syngeneic transplants). Cell sampling by bone marrow aspiration can provide further information on the function of the transplanted cells. These monitoring techniques may be enhanced by ex vivo labeling the cells to be transplanted (or some small fraction of such cells), thus permitting non-invasive monitoring of the location and movement of transplanted cells by nuclear magnetic resonance techniques. Non-myeloablative allogeneic transplantation (i.e. reduced-intensity transplant) is a similar cell therapy that can be effective for treating several types of cancer. Generally, this technique relies on a lower dose of radiation and/or chemotherapeutic and a limited graft-versus-host disease (the action of immune cells from the transplant against any residual host cancer cells) to provide sufficient anti-cancer activity, as well as the hematopoietic potential of the graft cells to restore the patient's hematopoietic system. As with a traditional ablative graft, the techniques of the present invention may be used to monitor the locations and movements of graft cells in a non-myeloablative allogeneic transplantation.

Cellular therapeutics are also in development for use in the delivery of therapeutic proteins. In one embodiment, cells can be isolated, grown in quantity ex vivo and then implanted to produce and secrete soluble factors, which may be active either locally (e.g. enzymes, cytokines, and neurotransmitters) or at a distance (e.g. hormones and growth regulators). Cells may also be administered to a patient in order to accomplish complex therapeutic purposes, such as reconstitution of tissues, organs, or immune responses based on their ability to home to specific sites within the body, exit from the circulation, and integrate into surrounding tissue or differentiate to replace damaged tissue. Stem cell therapies have also been proposed for myriad diseases including neurological disorders, particularly those characterized by cell death (e.g., Parkinson's disease, stroke and brain injury caused by trauma), cardiovascular disorders (e.g., myocardial infarction), muscle regeneration (e.g., in patients suffering from cachexia or other wasting disorders), pancreatic regeneration in diabetes, liver regeneration, etc. In each instance, cells, or a subpopulation thereof, may be labeled with an imaging reagent ex vivo prior to administration, thus allowing the monitoring of these cells in vivo. In vivo monitoring by a nuclear magnetic resonance technique may be useful, for example, to evaluate the viability of the administered cells. A doctor may tailor a dosing schedule depending on the degree to which labeled cells are detected in a patient after administration. In vivo monitoring may also be useful in determining whether therapeutic cells have localized to a desired location. In general, it will be possible to investigate correlations between the migration behavior of therapeutic cells in vivo, as well as the number and/or survivorship of therapeutic cells in vivo, and therapeutic outcomes. When such correlations have been established, the in vivo imaging of therapeutic cells may be used as a prognostic indicator that may be helpful in selecting the appropriate dosage, administration modes and additional therapeutic interventions that will benefit the patient. Certain imaging advances of the invention will benefit a broad range of cellular therapeutic strategies because these imaging methodologies will be able to detect when, where and if the therapeutic cells have been delivered to the desired targets in vivo.

One example of an application of technology disclosed herein is in tracking dendritic cells (DCs). DCs are known to be the most efficient antigen presenting cells and have the capacity to stimulate naive T cells to initiate an immune response. Because DCs are the most potent stimulators of immune response in the body, DCs represent a possible therapeutic approach to increasing the "visibility" of tumors to a patient's immune system. DCs are the focus of tumor vaccines in development. Varying methods are used to expose the dendritic cells to tumor antigens ex vivo, after which educated dendritic cells are reinfused to stimulate development of T-cell mediated tumor killing. In the Examples, below, applicants present data applying an embodiment of the present invention to the labeling and tracking of DCs.

In certain aspects, labeled cells are administered to a subject for non-therapeutic purposes. For example, cells may be labeled ex vivo, administered to a subject and then detected, with the expectation that the labeled cells will behave similarly to like, unlabeled cells in vivo and may therefore be used to monitor the behavior of endogenous cell populations. Monitoring may be used for the purpose of tracking movements of cells, particularly in the case of cells that are known to be highly mobile, such as cells of the immune system, many types of stem cells and blood born cells. Monitoring may also be used for the purpose of tracking viability or adherence of non-mobile cells at the site of implant. Cells of many tissues, such as muscle, liver, pancreas, kidney, brain or skin will tend to be relatively stationary, but disappearance of label may indicate a high death rate, low adherence, or other information. Modern cell culture and sorting techniques allow the selective pooling and labeling of virtually any desired cell population, including various stem cell types, immune cell types, and other blood cell types.

As an example, labeled immune cells may be used as detectable proxies for the movements of immune cells in a patient. Immune cells participate in and are markers for a host of inflammatory and autoimmune disorders, as well as cancer and atherosclerotic plaque formation. As a general methodology, any process involving the recruitment of immune cells may be detected in a patient by administering to the patient labeled immune cells. The accumulation of label in a particular area provides an indication of the degree of immune response occurring in that portion of the body. Traditionally, these types of studies involve histological techniques that are incompatible with living subjects. Certain methods of the invention may facilitate the development of therapeutic strategies for the treatment of human diseases. The ability to track selected populations of immune cells non-invasively, and without the use of radioisotopes, can impact many areas of basic and clinical immunology, such as multiple sclerosis, diabetes, monitoring organ transplant rejection, and cancer. For instance, tumors are often highly infiltrated by immune cells. Labeled cells may be imaged in a subject to reveal the location of a tumor, and in some instances may be useful as a non-invasive detection screen. Early detection of cancers has been a critical problem, as most early stage cancers are readily treated by surgery without resort to debilitating chemotherapeutic agents. Likewise, the progress of other inflammatory diseases may be monitored by tracking the dynamics of immune cells in the patient. The effectiveness of immunosuppressant therapy may be assessed as well. In the instance of an organ transplant recipient, the recipient could receive a dose of labeled immune cells prior to receiving the transplantation. In vivo monitoring of the accumulation of immune cells in the transplant could then be used as an early warning sign of rejection. In the case of transplants, the methods disclosed herein are particularly desirable because the alternative, biopsies, are well-known to increase the risk of organ rejection.

As an additional example, cells for use in a bone marrow cell transplant, or a peripheral blood stem cell transplant, may be labeled ex vivo as described herein, administered, and monitored in vivo by a nuclear magnetic resonance technique. Such monitoring may be used to evaluate the engraftment of donor cells in the recipient bone cavities, as well as survivorship and movement of labeled cells in the recipient. A physician can use information relating to the trafficking of donor cells in a recipient as an early indication of the likely success or failure of the procedure. This type of early detection will allow physicians to tailor the post-transplant therapeutic regimen accordingly. Another cellular cancer therapeutic where the detection technology can be applied is the allogeneic non-myeloablative, or reduced intensity transplant. This procedure may be used with a donor lymphocyte infusion to boost graft-versus-tumor effect which destroys cancer cells. Here the entire population, or a fraction, of transplanted cells could be labeled before infusion. A nuclear magnetic resonance technique could then be used determine where the cells traffic to in the body, which can be indicative of the efficacy of the procedure. As it is often desirable to limit the dose of allogeneic cells to minimize rejection, the cell's trafficking pattern may be used to calibrate dose. In the above cancer cell therapies it may be desirable to selectively label one or more sub-population of the transplanted cells (e.g., CD34+ stem cells or T-cells) that are believed to have therapeutic efficacy.

As a further example, cells involved in formation of new tissue, such as in angiogenesis, can be labeled, administered to a subject, and detected to identify hotspots of tissue formation. For example, smooth muscle cells and/or endothelial precursor cells may be labeled and introduced into the bloodstream. Such cells are expected to accumulate at sites of angiogenic activity. Angiogenic activity may be associated with physiological and pathological events such as menstrual cycling, early pregnancy, collateral vessel formation in response to arterial blockages, tumor development and wound healing. Similarly, cells involved in wound healing, such as fibroblasts, may be labeled and administered systemically or to a site of suspected injury in order to monitor cellular behavior.

In certain instances, cells may prove to be so thoroughly associated with a biological site or structure of interest that the labeled cells may be administered for the sole purpose of aiding in the visualization of such a structure. As mentioned above, immune cells characteristically infiltrate tumors. Accordingly, labeled immune cells may be administered for the purpose of visualizing tumors.

Technology disclosed herein may be applied to studies of animal models of human diseases. Various animal models of diseases may evince altered dynamics or survival of one or more cell populations. Such cell populations may be labeled, administered to the animal and monitored. For example, the infiltration of immune cells into the pancreas of the NOD mouse model for diabetes may be monitored. Other examples of animal models include: experimental allergic encephalomyelitis (multiple sclerosis model), gliosarcoma tumor models, and organ-transplant rejection. By tracking phenotypically-defined populations of immune cells in these models, one can elucidate aspects of the disease etiology and monitor how cell trafficking is affected by therapeutics. This method may be used, for example, to screen for drugs that have a desired effect in an animal model. A drug screening assay may comprise administering labeled cells to an animal and detecting the cells in vivo in the presence of a test agent. Changes in cell behavior that are correlated with the presence of the test agent may be indicative of a therapeutic effect. Such changes may be detected by comparison to a suitable reference, including, for example, the same animal before and after treatment with the test agent or a separate, untreated animal. In addition to a test agent, the methods may be used to evaluate the effects of test conditions, such as an exercise regimen, injury, genetic alteration, etc. As an example, it is expected that a drug for treatment of an autoimmune disease would decrease the tendency of immune cells to accumulate in an affected tissue. In addition to steady state evaluations, methods disclosed herein may be used to evaluate kinetic properties of cells, such as the rate at which cells arrive at a particular site and the time of signal persistence at a site. Drug screening assays may be particularly powerful when combined with in vivo monitoring of tightly defined cell populations, such as certain groups of immune cells that are implicated in various disorders. For example, monitoring of labeled cytotoxic T cells may be particularly useful in identifying drugs that may be useful in preventing transplant rejection. The ability to monitor cells in vivo provides a powerful new assay that may be applied to the analysis of essentially any experimental animal, including, for example, any of the various transgenic or otherwise mutant mice that have been generated.

Several groups have studied labeling and visualizing immune cells using MRI contrast agents. Other researchers have used MRI contrast agents to label cell types such as stem cells and neuronal precursors. The majority of these studies render the cells magnetically-distinct via the incorporation superparamagnetic iron-oxide (SPIO) agents. Cells labeled with contrast agents incorporating other types of metal ions, particularly gadolinium and manganese have also been used. In studies utilizing these metal-ion based agents, the compounds are not directly imaged; instead, one observes their indirect effect on surrounding waters. The presence of the agent tends to shorten the relaxation times ($T_1$, $T_2$, or $T_2^*$) of water in proximity to the compound; these effects can be detected in relaxation time-weighted images. SPIO agents, for example, impart contrast to conventional $^1H$ images by locally perturbing the magnetic field experienced by the nearby mobile water molecules, which in turn modulates $T_1$, $T_2$, or $T_2^*$. Methods described herein are distinctly different from methods using metal ion based contrast agents because signals from $^{19}$F nuclei in the imaging reagents may be directly detected and, optionally, imaged.

An inherent drawback to detecting labeled cells using metal-ion based contrast agents is that one is often in a situation where it is necessary to interpret subtle changes in grayscale contrast in regions that are believed to contain labeled cells. The large $^1$H background signal from the high concentration of mobile water present in tissues can make it difficult to unambiguously identify regions containing labeled cells; this is especially problematic if the labeled cell biodistribution is not known a priori. The results of a 'snapshot' image are often ambiguous as to whether labeled cells are present in a specific tissue. This is a particularly vexing problem when trying to detect SPIO labeled cells in iron-laden organs that intrinsically appear dark in anatomical ($T_2$- or $T_2^*$-weighted) images, such as in the liver or the spleen. Often one must resort to detecting the time-lapse image intensity changes in a particular organ over a period of several hours to verify that labeled cells have accumulated.

Thus the methods and compositions disclosed herein provide much needed tools in the fields of medicine and biology.

2. Imaging Reagents and Formulations

The imaging reagent used in the subject methods is a fluorocarbon, i.e., a molecule including at least one carbon-fluorine bond. By virtue of the $^{19}$F atoms, the imaging reagents disclosed herein may be detected by $^{19}$F MRI and other nuclear magnetic resonance techniques, such as MRS techniques. In certain preferred embodiments, a fluorocarbon imaging reagent will have one or more of the following properties: 1) tolerable cytotoxicity; 2) a $^{19}$F NMR spectrum that is simple, ideally having a single, narrow resonance to minimize chemical shift artifacts; 3) high sensitivity with a large number of NMR-equivalent fluorine atoms in each molecule; 4) formulated to permit efficient labeling of many cell types and not restricted to phagocytic cells.

Exemplary compounds include aryl or heteroaryl trifluoromethyl sulfonic acid esters (triflates) or sulfonamides (triflamides), esters of fluorinated alcohols (such as 2,2,2-trifluoroethanol, perfluoro-tert-butanol, and 2,2,3,3,3-pentafluoropropanol), esters and amides of perfluoroalkanoic acids (such as trifluoroacetic acid, perfluorotetradecanoic acid, and nonafluoropentanoic acid), ethers of perfluoroalkanes, and the like. Preferably, the imaging reagent comprises a plurality of fluorines bound to carbon, e.g., greater than 5, greater than 10, greater than 15 or greater than 20 fluorines bound to carbon. Preferably, at least 4, at least 8, at least 12 or at least 16 of the fluorines have a roughly equivalent NMR chemical shift.

In certain embodiments, the imaging reagent is a perfluoro crown ether, such as perfluoro-15-crown-5, perfluoro-18-crown-6, perfluoro-12-crown-4, etc., also referred to herein as cyclic perfluoropolyethers (cyclic PFPEs). Such compounds are advantageous in that the $^{19}$F nuclei of these molecules will have similar or identical NMR resonances, resulting in a higher signal-to-noise ratio image with a reduction in or absence of chemical-shift image artifacts. The macrocycle perfluoro-15-crown-5 ether has particularly preferable characteristics. It is neither lipophilic nor hydrophilic, which is typical for perfluoropolyethers, and is emulsified into aqueous solution. Typical emulsions are small particulates (~10-500 nm diameter) that are stable in aqueous solution and can be taken up by cells. One of skill in the art will recognize, that other fluorinated compounds will have desirable properties, particularly those fluorinate compounds in which each fluorine atom is in a similar chemical environment. Esters of perfluoro-tert-butanol, 1,3,5-tris(trifluoromethyl)benzene, hexafluoroacetone, poly(trifluoromethylethylene), and perfluorocyclohexane are examples of compounds having multiple fluorine atoms with $^{19}$F resonances that have the same, or nearly the same, Larmor frequencies.

In certain embodiments, the imaging reagent is a polymer. In certain embodiments, the imaging reagent is or includes a linear perfluoropolyether (linear PFPE), e.g., a compound having a structure or portion thereof comprising repeated units of —[O—CF$_2$(CF$_2$)$_x$CF$_2$]$_n$—, where x is an integer from 0 to 10, preferably from 0-3, and n is an integer from 2 to 100, preferably from 4 to 40. Perfluorinated linear polyethylene oxide, for example, can be obtained from Exfluor Corp. (Round Rock, Tex.). Either or both ends (or a plurality of ends, in the case of branched polymers) may be derivatized with a moiety that provides an additional desired functionality. For example, an imaging reagent may have a formula of A-B-C, where A and/or C may be a functional moiety and B comprises repeated units of —[O—CF$_2$(CF$_2$)$_x$CF$_2$]$_n$—, where x is an integer from 0 to 10, preferably from 0-3, and n is an integer from 2 to 100, preferably from 4 to 40. Functional moieties (e.g., non-fluorinated monomers conferring a particular desired function) are discussed further below.

A linear perfluoropolyether may also be described as a composition having the average formula:

XO(Y—O)$_n$Z wherein Y is selected from the group consisting of:

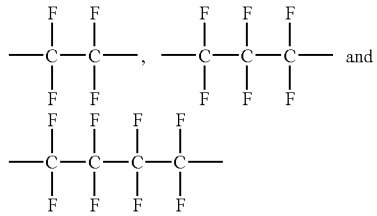

wherein n is an integer from 8 to 30; wherein X and Z are the same and are selected from the group consisting of perfluoroalkyls, perfluoroethers, fluoroalkyls terminated with fluoroacyl, carboxyl, amide or ester, methylols, acid chlorides, amides, amidines, acrylates and esters, as well as any of the preceding derivatized with a functional moiety.

While a completely fluorinated polymer can be formed, for example, by reacting a perfluorinated diacid with a perfluorinated dihalocarbon (such as 1,4-diiodooctafluorobutane), fluorinated monomers can be reacted with other monomers (optionally functional moieties, which may be non-fluorinated) to form hybrid polymers that are useful as imaging reagents. A variety of different non-fluorinated monomers can be used to vary the chemical and physical properties of the overall polymer, and make it possible to tailor the imaging reagent for specific uses. For example, a highly lipophilic imaging reagent may concentrate in adipocytes and other fatty tissues, while a highly hydrophilic imaging reagent may be useful for imaging the circulatory system or the lymph system.

For labeling cells, the imaging reagents can be employed in one or more of at least three modalities: 1) imaging reagents that are internalized or otherwise absorbed by target cells without the formation of any covalent or other binding association; 2) imaging reagents that covalently attach to target cells; and 3) imaging reagents coupled to molecules, such as antibodies or ligands, that bind to molecules present on the target cells.

Imaging reagents of the first type include the perfluoro crown ethers and other PFPEs that are taken up by cells and, preferably, are retained in the cell without degradation for a substantial period of time, e.g., having a half-life in the cell of at least 1 hour, at least 4 hours, at least about a day, at least about three days, or even at least about a week. For obvious reasons, it is preferred that the imaging reagent not interfere with ordinary cellular functions or exhibit cytotoxicity at the concentrations employed for labeling. As demonstrated herein, perfluoropolyethers show minimal toxic effect on the labeled cells.

Imaging reagents of the second type include electrophilic compounds that react with nucleophilic sites on the cell surface, such as exposed thiol, amino, and/or hydroxyl groups. Accordingly, imaging reagents such as maleimides, alkyl iodides, N-hydroxysuccinimide or N-hydroxysulfosuccinimide esters (NHS or sulfo-NHS esters), acyl succinimides, and the like can form covalent bonds with cell surfaces. Other techniques used in protein coupling can be adapted for coupling imaging reagents to cell surface proteins. See Means et al. (1990) *Bioconjugate Chemistry* 1:2-12, for additional approaches to such coupling.

Imaging reagents of the third type can be prepared by reacting imaging reagents of the second type not with the cells themselves, but with a functional moiety that is a cell-targeting ligand or antibody. Suitable ligands and antibodies can be selected for the application of interest. For example, a ligand that selectively targets hematopoietic cells could be labeled with an imaging reagent as described herein and administered to a patient, such as by injection.

Alternatively, an imaging reagent can be coupled to an indiscriminate internalizing peptide, such as antepennepedia protein, HIV transactivating (TAT) protein, mastoparan, melittin, bombolittin, delta hemolysin, pardaxin, Pseudomonas exotoxin A, clathrin, Diphtheria toxin, C9 complement protein, or a fragment of any of these. Cells treated with this indiscriminate molecule ex vivo will absorb the imaging reagent. When such labeled cells are implanted into an animal, such as a mammal, the imaging reagent can be used to visualize and/or track the implanted cells by nuclear magnetic resonance techniques.

In one embodiment, the internalizing peptide is derived from the drosophila antepennepedia protein, or homologs thereof. The 60-amino acid-long homeodomain of the homeo-protein antepennepedia has been demonstrated to translocate through biological membranes and can facilitate the translocation of heterologous polypeptides to which it is coupled. See for example Derossi et al. (1994) *J Biol Chem* 269:10444-10450; and Perez et al. (1992) *J Cell Sci* 102:717-722. It has been demonstrated that fragments as small as 16 amino acids long of this protein are sufficient to drive internalization. See Derossi et al. (1996) *J Biol Chem* 271:18188-18193.

Another example of an internalizing peptide is the HIV transactivator (TAT) protein. This protein appears to be divided into four domains (Kuppuswamy et al. (1989) *Nucl. Acids Res.* 17:3551-3561). Purified TAT protein is taken up by cells in tissue culture (Frankel and Pabo, (1989) *Cell* 55:1189-1193), and peptides, such as the fragment corresponding to residues 37-62 of TAT, are rapidly taken up by cell in vitro (Green and Loewenstein, (1989) *Cell* 55:1179-1188). The highly basic region mediates internalization and targeting of the internalizing moiety to the nucleus (Ruben et al., (1989) *J. Virol.* 63:1-8). Peptides or analogs that include a sequence present in the highly basic region, such as CFITKALGISYGRKKRRQRRRPPQGS, can be conjugated to fluorinated imaging reagents to aid in internalization and targeting those reagents to the intracellular milieu.

Another PFPE composition of interest is linear PFPEs derivatized with a variety of end groups. The linear compounds have the advantage that one can conjugate a variety of functional entities to the end groups, such as functional moieties of various types. The $^{19}F$ NMR spectra of these linear compounds generally is more complex than the macrocyclic compounds, but a PFPE with two well-separated NMR signals can also be used. In this case it may be desirable to use an MRI pulse sequence that incorporates one or more off-resonance saturation pulses applied to the smaller resonance to eliminate any chemical shift artifacts.

A particularly useful application of linear PFPEs is the synthesis of a "dual mode" agent that can be detected by $^{19}F$ nuclear magnetic resonance techniques and includes a detection moiety that facilitates detection by a second detection method. As an example, a fluorescent moiety attached to the endgroups may be used to generate imaging reagents that can be visualized with $^{19}F$ MRI and fluorescence microscopy. A wide range of fluorescent moieties may be used in a dualmode agent. Many suitable fluorophores are known, including fluorescein, lissamine, phycoerythrin, rhodamine (Perkin Elmer Cetus), Cy2, Cy3, Cy3.5, Cy5, Cy5.5, Cy7, Fluor X (Amersham). Fluorescent moieties include derivatives of fluorescein, benzoxadioazole, coumarin, eosin, Lucifer Yellow, pyridyloxazole and rhodamine. These and many other exemplary fluorescent moieties may be found in the Handbook of Fluorescent Probes and Research Chemicals (2000, Molecular Probes, Inc.). Additional fluorescent moieties include fluorescent nanocrystals, such as the "quantum dot" products available from Quantum Dot Corporation (Hayward, Calif.). Such nanocrystals may be constructed with a semiconductor core having an appropriate emission spectrum (e.g., CdS, CdSe, CdTe), a shell composed of a non-emissive transparent and relatively non-reactive material that can be efficiently wed to the underlying core material (e.g., ZnS), and a coating that provides desirable solubility (e.g., for solubility in aqueous, physiological solutions) and possible reactive groups for attachment to a fluorocarbon described herein.

Dual mode imaging reagents that permit fluorescent detection are particularly useful in a variety of applications. For example, fluorescent labeling permits the use of fluorescence-based cell sorting mechanisms, such as Fluorescence Activated Cell Sorting (FACS). Cell sorting may be desirable, for example, to enrich for a population of cells that have been successfully labeled. This may be particularly useful where labeling has been directed to rarer cell populations. Dual mode agents are also useful for finding and characterizing labeled cells after they have been implanted into a living subject. In this application, cells may be biopsied, or by some other means harvested, from the subject after they have resided there for some duration. Biological analysis of the harvested cells can then be performed. For example, FACS analysis can be performed on the harvested cells, where after positively selecting cells for the fluorescent PFPE label, the cells can be assayed for the expression of specific cell surface markers (using a different color fluorescent probe) to investigate any change in cell phenotype that occurred following implantation. Fluorescent labels may also be used for fluorescence microscopy of cells, particularly using three-dimensional confocal fluorescence microscopy. Fluorescence microscopy will not generally be useful for in vivo visualization of deep tissues containing labeled cells, but surface tissues may be visualized as well as tissue samples. Dual labeling will be particularly valuable in calibrating and validating any new fluorocarbon-based nuclear magnetic resonance labeling method. Results obtained by, for example, MRI/MRS may be compared to those obtained by fluorescence detection, both in cultured labeled cells (biopsied or otherwise) and in vivo, to the extent possible. A known fluorescence signal strength per unit molecule may be used to calibrate MR/MRS measurements.

Detection moieties suitable for PET imaging may also be used to create dual mode imaging reagents that are detectable by nuclear magnetic resonance techniques and by PET techniques. For example, the $^{18}F$ isotope is a potent label for PET detection methods. A fluorocarbon imaging reagent may comprise a mixture of $^{18}F$ and $^{19}F$ isotopes, thus providing a dual mode label that is suitable for MRI/MRS and PET. $^{18}F$ and $^{19}F$ may also be added in separate monomers to form a mixed copolymer, or $^{18}F$ portions may be located at either end of a linear polyether, at the position where most other functional moieties would be added. $^{18}F$ has no NMR signal and so may be added at positions that would, for example, tend to decrease NMR linewidth, simplify the NMR spectrum, or alleviate chemical shifts from resonances that adversely effect the read-out obtained by a nuclear magnetic resonance technique. In addition, molecules of the fluorocarbon imaging reagents can incorporate other radioisotopes that are effective PET probes, such as $^{11}C$, $^{15}O$, and $^{13}N$. Those skilled in the art can, in view of this specification, devise many other PET-detectable moieties that can be incorporated into or, for example, attached to an endgroup(s), of the imaging reagents of this invention.

In certain embodiments, a linear perfluoropolyether may be derivatized with a relatively hydrophilic moiety at one, or preferably, both ends. For example, the hydrophilic moiety may be a polyethylene glycol, thus forming a tri-block copolymer with water-soluble regions on each end and a hydrophobic region in the center. When mixed in an aqueous environment, imaging reagents of this type will tend to form micelles, with the PFPE core surrounded by a water-soluble coat. Amino-PEG blocks are commercially available with a range of molecular weights. Coupling the PFPE core with other groups, such as aliphatic amines (see, e.g., FIG. 14, Rxn 2 and 4a) and phosphatidyl ethanolamine (see, e.g., FIG. 14, Rxn 3) in place of the hydrophilic sections, will give derivatives with different solubility characteristics.

In certain embodiments, the invention provides formulations of imaging reagents that are suitable for uptake by cells. Emulsions comprising a fluorocarbon imaging reagent, such as a PFPE, will preferably have a distribution of particle sizes that allow adequate cellular uptake. For example, it will generally be desirable that the mean particle size fall within a range from 10 nm to 500 nm, and preferably a range of from 30 nm to 150 nm or a range of from about 350 to 500 nm. Optionally, 25%, 50%, 75% or more of the particles will also fall within the selected range. Particle sizes may be evaluated by, for example, light scattering techniques or by visualizing the emulsion particles using EM micrographs. In certain cell types that have a relatively small amount of cytoplasm, such as most stem cells, preferred particle sizes will be in the range of 10-50 nm in diameter. Emulsions for use in cells should preferably be stable at a wide range of temperatures. For example, it will often be desirable to store the emulsion at a cool temperature, in the range of 2-10° C., and preferably 4° C., and then warm the emulsion to room temperature (e.g., 18 to 28° C., and more typically 20 to 25° C.). After labeling of cells, the emulsion will experience a temperature of about 37° C. Accordingly, a preferred emulsion will retain the desired range of particle sizes at temperatures ranging from refrigeration temperatures up to body temperature. The surfactant may be designed to form stable emulsions that carry a large quantity of PFPE into the aqueous phase. Additionally, it may have properties that increase the intracellular delivery of the emulsion particles in the shortest possible incubation time. Increasing the PFPE intracellular loading improves sensitivity to the labeled cells. Furthermore, decreasing the incubation time can be important when working with the primary cells cultures because the cell phenotype may evolve over time. The efficiency of intracellular uptake depends on cell type. For example macrophages and dendritic cells will endocytose almost any particulate, whereas other cell types of interest may only be weakly phagocytic. In either case the uptake efficiency can be boosted substantially by incorporating cationic lipids into the surfactant, by using peptides (e.g. oligo-Arg9 and TAT-like peptides), or by incorporating antibodies that target specific cell surface molecules.

The properties of an emulsion may be controlled primarily by the properties of the imaging reagent itself, the nature of surfactants and/or solvents used, and the processing (e.g., sonication, etc.). Methods for forming PFPE emulsions are extensively described in U.S. Pat. Nos. 5,330,681 and 4,990,283. A continuous phase of a polyhydroxylated compound, such as polyalcohols and saccharides in concentrated aqueous solution may be effective. The following polyalcohols and saccharides have proved to be particularly effective: glycerol, xylitol, mannitol, sorbitol, glucose, fructose, saccharose, maltitol, dimer compounds of glycerol (di-glycerol or bis(2,3-di-hydroxypropyl)ether, solid water soluble polyhydroxylated compounds as sugars and glycerol condensation products as triglycerol and tetraglycerol. The dispersion in emulsion may be performed in the presence of conventional surfactants, including cationic, anionic, amphoteric and non-ionic surfactants, with ionic surfactants being preferable. Examples of suitable surfactants include sodium lauryl sulphate, sulphosuccinate (sulphosuccinic hemiester), coco-amphocarboxyglycinate, potassium cetyl phosphate, sodium alkyl-polyoxyethylene-ether carboxylate, potassium benzalconium chloride, alkyl amidopropyl betaine, cetyl-stearilic ethoxylated alcohol, and sorbitan-ethoxylate(20)-mono-oleate Tween 20. While thermodynamic equations may be used to attempt to predict mixtures of imaging reagents that will give emulsions having the desired particle sizes and stability, it is generally accepted that actual testing of various mixtures will be most effective. The emulsification of mixtures is simple and quick, permitting rapid testing of a wide range of combinations to identify those that give rise to emulsions that are suitable for use in the methods disclosed herein.

3. Cells and Labeling

Methods described herein may be used with a wide range of cells, including both prokaryotic and eukaryotic cells, and preferably mammalian cells.

Technologies for cell preparation include cell culture, cloning, nuclear transfer, genetic modification and encapsulation.

A partial list of suitable mammalian cells includes: blood cells, myoblasts, bone marrow cells, peripheral blood cells, umbilical cord blood cells, cardiomyocytes (and precursors thereof), chondrocytes (cartilage cells), dendritic cells, fetal neural tissue, fibroblasts, hepatocytes (liver cells), islet cells of pancreas, keratinocytes (skin cells) and stem cells. In certain preferred embodiments, the cells to be used are a fractionated population of immune cells. Recognized subpopulations of immune cells include the lymphocytes, such as B lymphocytes (Fc receptors, MHC class II, CD19+, CD21+), helper T lymphocytes (CD3+, CD4+, CD8−), cytolytic T lymphocytes (CD3+, CD4−, CD8+), natural killer cells (CD16+), the mononuclear phagocytes, including monocytes, neutrophils and macrophages, and dendritic cells. Other cell types that may be of interest include eosinophils and basophils.

Cells may be autologous (i.e., derived from the same individual) or syngeneic (i.e., derived from a genetically identical individual, such as a syngeneic littermate or an identical twin), although allogeneic cells (ie., cells derived from a genetically different individual of the same species) are also contemplated. Although less preferred, xenogeneic (ie., derived from a different species than the recipient) cells, such as cells from transgenic pigs, may also be administered. When the donor cells are xenogeneic, it is preferred that the cells are obtained from an individual of a species within the same order, more preferably the same superfamily or family (e.g. when the recipient is a human, it is preferred that the cells are derived from a primate, more preferably a member of the superfamily Hominoidea).

Cells may, where medically and ethically appropriate, be obtained from any stage of development of the donor individual, including prenatal (e.g., embryonic or fetal), infant (e.g., from birth to approximately three years of age in humans), child (e.g. from about three years of age to about 13 years of age in humans), adolescent (e.g., from about 13 years of age to about 18 years of age in humans), young adult (e.g., from about 18 years of age to about 35 years of age in humans), adult (from about 35 years of age to about 55 years of age in humans) or elderly (e.g., from about 55 years and beyond of age in humans).

In many embodiments, cells are labeled by contacting the cells with an emulsion of the imaging reagent, such that the reagent is taken up by cells. Both phagocytic and non-phagocytic cells may be labeled by such a method. For example, as demonstrated herein, both dendritic cells (phagocytic) and gliosarcoma cells (non-phagocytic) can be labeled by contacting the cells with an emulsion of the imaging reagent.

In certain embodiments the cells to be labeled are stem cells. Stem cell therapies are commonly used as part of an ablative regimen for treatment of cancer with high dose radiation and/or chemotherapeutic agents. Ablative regimens generally employ hematopoietic stem cells, or populations of cells containing hematopoietic stem cells, as may be obtained, for example, from peripheral blood, umbilical cord blood or bone marrow. Cells of this type, or a portion thereof, may be labeled and tracked in vivo to monitor survival and engraftment at the appropriate location. Other types of stem cells are increasingly attractive as therapeutic agents for a wide variety of disorders.

As an example, cells may be mouse embryonic stem cells, or ES cells from another model animal. The labeling of such cells may be useful in tracking the fate of such cells administered to mice, optionally as part of a preclinical research program for developing embryonic stem cell therapeutics. Examples of mouse embryonic stem cells include: the JM1 ES cell line described in M. Qiu et al., Genes Dev 9, 2523 (1995), and the ROSA line described in G. Friedrich, P. Soriano, Genes Dev 5, 1513 (1991), and mouse ES cells described in U.S. Pat. No. 6,190,910. Many other mouse ES lines are available from Jackson Laboratories (Bar Harbor, Me.). Examples of human embryonic stem cells include those available through the following suppliers: Arcos Bioscience, Inc., Foster City, Calif., CyThera, Inc., San Diego, Calif., BresaGen, Inc., Athens, Ga., ES Cell International, Melbourne, Australia, Geron Corporation, Menlo Park, Calif., Göteborg University, Göteborg, Sweden, Karolinska Institute, Stockholm, Sweden, Maria Biotech Co. Ltd.—Maria Infertility Hospital Medical Institute, Seoul, Korea, MizMedi Hospital—Seoul National University, Seoul, Korea, National Centre for Biological Sciences/Tata Institute of Fundamental Research, Bangalore, India, Pochon CHA University, Seoul, Korea, Reliance Life Sciences, Mumbai, India, Technion University, Haifa, Israel, University of California, San Francisco, Calif., and Wisconsin Alumni Research Foundation, Madison, Wis. In addition, examples of embryonic stem cells are described in the following U.S. patents and published patent applications: U.S. Pat. Nos. 6,245,566; 6,200,806; 6,090,622; 6,331,406; 6,090,622; 5,843,780; 20020045259; 20020068045. In preferred embodiments, the human ES cells are selected from the list of approved cell lines provided by the National Institutes of Health and accessible at http://escr.nih.gov. In certain preferred embodiments, an embryonic stem cell line is selected from the group consisting of: the WA09 line obtained from Dr. J. Thomson (Univ. of Wisconsin) and the UC01 and UC06 lines, both on the current NIH registry.

In certain embodiments, a stem cell for use in disclosed methods is a stem cell of neural or neuroendocrine origin, such as a stem cell from the central nervous system (see, for example U.S. Pat. Nos. 6,468,794; 6,040,180; 5,753,506; 5,766,948), neural crest (see, for example, U.S. Pat. Nos. 5,589,376; 5,824,489), the olfactory bulb or peripheral neural tissues (see, for example, Published US Patent Applications 20030003574; 20020123143; 20020016002 and Gritti et al. J Neurosci 22(2):437-45), the spinal cord (see, for example, U.S. Pat. Nos. 6,361,996, 5,851,832) or a neuroendocrine lineage, such as the adrenal gland, pituitary gland or certain portions of the gut (see, for example, U.S. Pat. No. 6,171,610 and PC12 cells as described in Kimura et al. 1994 J. Biol. Chem. 269: 18961-67). In preferred embodiments, a neural stem cell is obtained from a peripheral tissue or an easily healed tissue, thereby providing an autologous population of cells for transplant.

Hematopoietic or mesenchymal stem cells may be employed in certain disclosed methods. Recent studies suggest that marrow-derived hematopoietic (HSCs) and mesenchymal stem cells (MSCs), which are readily isolated, have a broader differentiation potential than previously recognized. Purified HSCs not only give rise to all cells in blood, but can also develop into cells normally derived from endoderm, like hepatocytes (Krause et al., 2001, Cell 105: 369-77; Lagasse et al., 2000 Nat Med 6: 1229-34). Similarly, HSCs from peripheral blood and from umbilical cord blood are expected to provide a useful spectrum of developmental potential. MSCs appear to be similarly multipotent, producing progeny that can, for example, express neural cell markers (Pittenger et al., 1999 Science 284: 143-7; Zhao et al., 2002 Exp Neurol 174: 11-20). Examples of hematopoietic stem cells include those described in U.S. Pat. Nos. 4,714,680; 5,061,620; 5,437,994; 5,914,108; 5,925,567; 5,763,197; 5,750,397; 5,716,827; 5,643,741; 5,061,620. Examples of mesenchymal stem cells include those described in U.S. Pat. Nos. 5,486,359; 5,827, 735; 5,942,225; 5,972,703, those described in PCT publication nos. WO 00/53795; WO 00/02654; WO 98/20907, and those described in Pittenger et al. and Zhao et al., supra.

Stem cell lines are preferably derived from mammals, such as rodents (e.g. mouse or rat), primates (e.g. monkeys, chimpanzees or humans), pigs, and ruminants (e.g. cows, sheep and goats), and particularly from humans. In certain embodiments, stem cells are derived from an autologous source or an HLA-type matched source. For example, stem cells may be obtained from a subject in need of pancreatic hormone-producing cells (e.g. diabetic patients in need of insulin-producing cells) and cultured to generate autologous insulin-producing cells. Other sources of stem cells are easily obtained from a subject, such as stem cells from muscle tissue, stem cells from skin (dermis or epidermis) and stem cells from fat.

In some preferred embodiments, cells for administration to a human should be compliant with good tissue practice guide-lines set by the U.S. Food and Drug Administration (FDA) or equivalent regulatory agency in another country. Methods to develop such a cell line may include donor testing, and avoidance of exposure to non-human cells and products.

Cells derived from a donor (optionally the patient is the donor) may be administered as unfractionated or fractionated cells, as dictated by the purpose of the cells to be delivered. Cells may be fractionated to enrich for certain cell types prior to administration. Methods of fractionation are well known in the art, and generally involve both positive selection (i.e., retention of cells based on a particular property) and negative selection (i.e., elimination of cells based on a particular property). As will be apparent to one of skill in the art, the particular properties (e.g., surface markers) that are used for positive and negative selection will depend on the desired population of cells. Methods used for selection/enrichment of cells may include immunoaffinity technology or density centrifugation methods. Immunoaffinity technology may take a variety of forms, as is well known in the art, but generally utilizes an antibody or antibody derivative in combination with some type of segregation technology. The segregation technology generally results in physical segregation of cells bound by the antibody and cells not bound by the antibody, although in some instances the segregation technology which kills the cells bound by the antibody may be used for negative selection.

Any suitable immunoaffinity technology may be utilized for selection/enrichment of the selected cells to be used, including fluorescence-activated cell sorting (FACS), panning, immunomagnetic separation, immunoaffinity chromatography, antibody-mediated complement fixation, immunotoxin, density gradient segregation, and the like. After processing in the immunoaffinity process, the desired cells (the cells bound by the immunoaffinity reagent in the case of positive selection, and cells not bound by the immunoaffinity reagent in the case of negative selection) are collected and either subjected to further rounds of immunoaffinity selection/enrichment, or reserved for administration to the patient.

Immunoaffinity selection/enrichment is typically carried out by incubating a preparation of cells comprising the desired cell type with an antibody or antibody-derived affinity reagent (e.g., an antibody specific for a given surface marker), then utilizing the bound affinity reagent to select either for or against the cells to which the antibody is bound. The selection process generally involves a physical separation, such as can be accomplished by directing droplets containing single cells into different containers depending on the presence or absence of bound affinity reagent (FACS), by utilizing an antibody bound (directly or indirectly) to a solid phase substrate (panning, immunoaffinity chromatography), or by utilizing a magnetic field to collect the cells which are bound to magnetic particles via the affinity reagent (immunomagnetic separation). Alternately, undesirable cells may be eliminated from the preparation using an affinity reagent which directs a cytotoxic insult to the cells bound by the affinity reagent. The cytotoxic insult may be activated by the affinity reagent (e.g., complement fixation), or may be localized to the target cells by the affinity reagent (e.g., immunotoxin, such as ricin B chain).

Although it is expected that methods disclosed herein will be frequently used for in vivo monitoring of cells, it should be noted that the methodologies are equally effective for the monitoring of cells in culture, in a tissue sample or other ex vivo cellular material. For therapeutic uses, cells may be labeled at a desired step during the preparation for administration to the patient.

A variety of methods may be used to label cells with imaging reagent. In general, cells will be placed in contact with imaging reagent such that the imaging reagent becomes associated with the cell. Conditions will often be standard cell culture conditions designed to maintain cell viability. The term "associated" is intended to encompass any manner by which the imaging reagent and cell remain in sufficiently close physical proximity for a sufficient amount of time as to allow the imaging reagent to provide useful information about the position of the cell, whether in vivo or in vitro. Imaging reagent may be located intracellularly, e.g. after phagocytosis or surfactant mediated entry into the cell. Immune cells, such as dendritic cells, macrophages and T cells are highly phagocytic and data presented herein and in other studies demonstrate that such cells, and other phagocytic cell types, are readily labeled. One study [21] in the experimental allergic encephalomyelitis (EAE) animal model showed that monocytes, labeled in situ following a bolus injection of emulsified PFPE, could be detected in the CNS using $^{19}$F MRI. Other cell types, such as stem cells may also be labeled, regardless of phagocytic activity. Imaging reagent may be inserted into a cell membrane or covalently or non-covalently bound to an extracellular component of the cell. For example, certain linear fluorocarbons described herein may be derivatized to attach one or more targeting moiety. A targeting moiety will be selected to facilitate association of the imaging reagent with the cell to be labeled. A targeting moiety may be designed to cause non-specific insertion of the fluorocarbon into a cell membrane (e.g., a hydrophobic amino acid sequence or other hydrophobic moiety such as a palmitoyl moiety or myristoyl moiety) or to facilitate non-specific entry into the cell. A targeting moiety may bind to a cell surface component, as in the case of receptor ligands. A targeting moiety may be a member of a specific binding pair, where the partner is a cell surface component. The targeting moiety may be, for example, a ligand for a receptor, or an antibody, such as a monoclonal or polyclonal antibody or any of the various polypeptide binding agents comprising a variable portion of an immunoglobulin (e.g., Fv fragment, single chain Fv (scFv) fragment, Fab' fragment, F(ab')2 fragment, single domain antibody, camelized antibody, humanized antibody, diabodies, tribodies, tetrabodies).

Where cells are to be used in a therapeutic regimen, various methods have been used to for delivery of cells including injections and use of special devices to implant cells in various organs. The present invention is not tied to any particular delivery method. Data presented herein demonstrate that labeled cells may be monitored regardless of whether the cells are delivered directly to a particular site or delivered systemically. Labeled DCs were successfully imaged following either a focal implantation directly into tissues or an intravenous injection. Cells may be inserted into a delivery device which facilitates introduction by injection or implantation into the subjects. Such delivery devices may include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The cells may be prepared for delivery in a variety of different forms. For example, the cells may be suspended in a solution or gel or embedded in a support matrix when contained in such a delivery device. Cells may be mixed with a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention may be prepared by incorporating cells as described herein in a pharmaceutically acceptable carrier or diluent and, as required, other ingredients enumerated above, followed by filtered sterilization.

4. Nuclear Magnetic Resonance Techniques

As described herein, nuclear magnetic resonance techniques may be used to detect populations of labeled cells. The term "detect" is used to include any effort to ascertain the presence or absence of a labeled molecule or cell, particularly by a nuclear magnetic resonance technique. The term "detect" is also intended to include more sophisticated measurements, including quantitative measurements and two- or three-dimensional image generation. For example, MRI may be used to generate images of such cells. In many instances, the labeled cells may be administered to a living subject. Following administration of the cells, some portion of the subject, or the entire subject, may be examined by MRI to generate an MRI data set. A "data set", as the term is used herein, is intended to include raw data gathered during magnetic resonance probing of the subject material, as well as information processed, transformed or extracted from the raw data. Examples of processed information include two-dimensional or three-dimensional pictorial representations of the subject material. Another example of extracted information is a score representing the amount or concentration of imaging reagent or $^{19}$F signal in the subject material. For example, the signal-to-noise-ratio (SNR) of the $^{19}$F signal may be measured and used to calculate the abundance of labeled cells. This type of data may be gathered at a single region of the subject, such as, for example, the spleen or another organ of particular relevance to the labeled cells. Labeled cells may be examined in contexts other than in the subject. It may be desirable to examine labeled cells in culture. In certain embodiments, labeled cells may be applied to or generated within a tissue sample or tissue culture, and labeled cells may therefore be imaged in those contexts as well. For example, an organ, tissue or other cellular material to be transplanted may be contacted with an imaging reagent to generate labeled cells prior to implantation of such transplant in a subject.

In general, labeling agents of the invention are designed for use in conventional MRI detection systems. In the most common implementation of MRI, one observes the hydrogen nucleus (proton, $^{1}$H) in molecules of mobile water contained in subject materials. To detect labels disclosed herein, an alternate nucleus is detected, $^{19}$F. $^{19}$F MRI has only slightly less intrinsic sensitivity compared to $^{1}$H; the relative sensitivity is approximately 0.83. Both have a spin of +½. The natural isotopic abundance of $^{19}$F is 100%, which is comparable to 99.985% for $^{1}$H. The physical principles behind the detection and image formation are the same for both $^{1}$H and $^{19}$F MRI. The subject material is placed in a large static magnetic field. The field tends to align the magnetic moment associated with the $^{1}$H or $^{19}$F nuclei along the field direction. The nuclei are perturbed from equilibrium by pulsed radiofrequency (RF) radiation at the Larmor frequency, which is a characteristic frequency proportional to the magnetic field strength where nuclei resonantly absorb energy. Upon removing the RF, the nuclei induce a transient voltage in a receiver antenna; this transient voltage constitutes the nuclear magnetic resonance (NMR) signal. Spatial information is encoded in both the frequency and/or phase of the NMR signal by selective application of magnetic field gradients that are superimposed onto the large static field. The transient voltages are generally digitized, and then these signals may be processed by, for example, using a computer to yield images.

At constant magnetic field strength, the Larmor frequency of $^{19}$F is only slightly lower (~6%) compared to $^{1}$H. Thus, it is straightforward to adapt conventional MRI scanners, both hardware and software, to acquire $^{19}$F data. The $^{19}$F detection may be coupled with different types of magnetic resonance scans, such as MRI, MRS or other techniques. Typically, it will be desirable to obtain a $^{1}$H MRI image to compare against the $^{19}$F image. In a living organism or other biological tissue, the proton MRI will provide an image of the subject material and allow one to define the anatomical context of the labeled cells detected in the $^{19}$F image. In a preferred embodiment of the invention, data is collected for both $^{19}$F and $^{1}$H during the same session; the subject is not moved during these acquisitions to better ensure that the two data sets are in spatial registration. Normally, $^{19}$F and $^{1}$H data sets are acquired sequentially, in either order. Alternatively, with appropriate modifications to the hardware and/or software of the MRI instrument, both data sets can be acquired simultaneously, for example, to conserve imaging time. Other imaging techniques, such as fluorescence detection may be coupled with $^{19}$F MRI. This will be particularly desirable where a fluorocarbon imaging reagent has been derivatized with a fluorescent moiety.

MRI examination may be conducted according to any suitable methodology known in the art. Many different types of MRI pulse sequences, or the set of instructions used by the MRI apparatus to orchestrate data collection, and signal processing techniques (e.g. Fourier transform and projection reconstruction) have been developed over the years for collecting and processing image data (for example, see *Magnetic Resonance Imaging, Third Edition*, editors D. D. Stark and W. G. Bradley, Mosby, Inc., St. Louis Mo. 1999). The reagents and methods of this invention are not tied to any particular imaging pulse sequence or processing method of the raw NMR signals. For example, MRI methods that can be applied to this invention broadly encompasses spin-echo, stimulated-echo, gradient-echo, free-induction decay based imaging, and any combination thereof. Fast imaging techniques, where more than one line in k-space or large segments of k-space are acquired from each excited signal, are also highly suitable to acquire the $^{19}$F (or $^{1}$H) data. Examples of fast imaging techniques include fast spin-echo approaches (e.g. FSE, turbo SE, TSE, RARE, or HASTE), echo-planar imaging (EPI), combined gradient-echo and spin-echo techniques (e.g. GRASE), spiral imaging, and burst imaging. The development of new and improved pulse sequence and signal processing methods is a continuously evolving field, and persons skilled in the art can devise multiple ways to image the $^{19}$F labeled cells in their anatomical context.

As another example of a nuclear magnetic resonance technique, MRS can be used to detect the presence of fluorocarbon-labeled cells in localized tissues or organs. Normally MRS methods are implemented on a conventional MRI scanner. Often the localized volume of interest (VOI) is defined within a conventional anatomical $^{1}$H MRI scan. Subsequentially the magnitude of the $^{19}$F NMR signal observed within the VOI is directly related to the number of labeled cells, and/or the mean concentration of PFPE per cell present in the tissue or organ. Methods for isolating a VOI within a much larger subject are well known the art (for example, *Magnetic Resonance Imaging, Third Edition*, Chapter 9, Editors D. D. Stark and W. G. Bradley, Mosby, Inc., St. Louis Mo. 1999). Examples include using a localized RF surface coil near the VOI, surface spoiling, surface coil $B_1$-gradient methods, slice-selective $B_0$-gradient techniques, STEAM, PRESS, image selective in vivo spectroscopy (ISIS), and magnetic resonance spectroscopic imaging (MRSI). The development of new and improved pulse sequence and signal processing methods is continuously evolving for MRS, and persons skilled in the art can devise multiple ways to detect the $^{19}$F NMR signals emanating from the fluorocarbon labeled cells in VOIs.

The application will be more readily understood by reference to the following examples, which are included merely for purposes of illustration of certain aspects and embodiments of the present application, and are not intended to limit the application.

EXAMPLES

In this section, data demonstrating the feasibility of the invention is presented. The exemplary embodiment of the invention uses fluorine-based imaging reagents to label cultured cells. Labeled cells are introduced into a living subject and tracked in vivo using $^{19}$F MRI. $^{19}$F MRI images are overlaid with $^1$H MRI images to establish the anatomical location of the labeled cells.

1. NMR Properties of PFPE-Labeled Dendritic Cells

These data demonstrate in vitro labeling of immune cells with PFPE. Dendritic cells (DCs) from a fetal-skin-derived cell line (FSDCs) [24] were incubated under physiological conditions for 4 hours in culture media (containing RPMI-1640, 10% fetal bovine serum, 100 μg/mL streptomycin, 100 U/mL penicillin, and 2 mM glutamine) with the PFPE (i.e. perfluoro-15-crown-5 ether) emulsion particles. The cells were then thoroughly washed of excess PFPE, and $3\times10^6$ cells were placed in a NMR capillary tube. A typical $^{19}$F NMR spectrum from the labeled FSDCs is shown in FIG. 1. This spectrum was obtained at (282 MHz) using a standard high-resolution NMR spectrometer. A single NMR peak was observed from the PFPE in the DCs with good a signal-to-noise ratio (FIG. 1). The NMR linewidth (full-width at half-maximum) is 150 Hz, which is sufficiently narrow for MRI applications. A reference $^{19}$F compound (trifluoroacetic acid) was placed in a separate tube next to the capillary containing the DCs (FIG. 1). By comparing the integrated areas under the two peaks one can quantify the total number of PFPE molecules taken up by the cells. Other cell types have been labeled with PFPE, and similar results were obtained. FIG. 1b shows $^{19}$F NMR spectra for rat 9 L gliosarcoma cells, T-cell enriched spleenocytes, and macrophages labeled with PFPE. Data in FIG. 1b were obtained using similar labeling and measurement procedures as (a). The rat 9 L gliosarcoma cells (ATCC, Manassas, Va.) were cultured in Dulbecco's Modified Eagle Medium (DMEM) enriched with 10% FBS, 2 mM L-glutamine, 100 U/ml penicillin, and 100 μg/ml streptomycin. The PFPE was pre-mixed with Lipofectamine, and then added to the cell culture and incubated for 4 hours. Cells were thoroughly washed, pelleted, and assayed with $^{19}$F NMR (FIG. 1b). T-cell enriched splenocytes were obtained from a C57BL/6 J mouse. The spleen was harvested, crushed between glass slides, and suspended in RPMI with 5% FBS. Red cells were removed. T-cell enrichment was achieved by incubating cells on a prepared nylon column to remove adherent cells. Remaining cells were labeled with PFPE in suspension by incubating the emulsion at physiological conditions in RPMI with 10% FBS for 3 hours. No Lipofectamine was used for these cells. Cells were then collected and loaded into a centrifuge tube with a Ficoll solution to clean the cell suspension of any remaining PFPE. After centrifugation, the cells pellet on the bottom of the tube and the PFPE remains in the Ficoll. The cell pellet was recovered and assayed with $^{19}$F NMR. Macrophages where an adherent EOC-20 mouse cell line (ATCC); these were cultured in supplemented DMEM media according to the supplier's instructions. PFPE was added to the culture media and incubated overnight. Cells were then washed thoroughly, harvested, and pelleted for $^{19}$F NMR. As was the case with the T-cells, no Lipofectamine was used in labeling the macrophages, as these cells are highly phagocytic and readily take up the emulsion particles.

Applicants have successfully labeled several different types of DCs, including bone-marrow-derived DCs (BM-DCs) and DCs from a fetal skin-derived cell line [24] (FS-DCs). Applicants have also successfully labeled macrophages, T-cells, and gliasarcoma cells and the results indicate that the labeling efficiency is comparable to what is observed in the DCs. $^{19}$F NMR spectra taken in intact cell suspensions have been used to confirm intracellular PFPE labeling and to quantify the amount of uptake.

2. In Vitro MRI of PFPE-Labeled DCs

Figure 2:
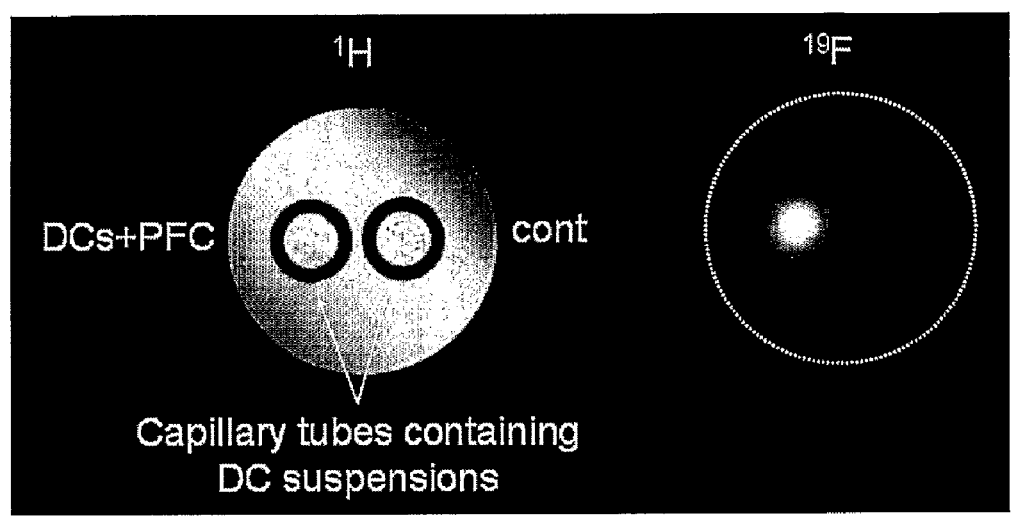
FIG. 2. In vitro MRI of capillary tubes containing PFPE-labeled DCs (DCs+PFPE) and unlabeled DCs (cont). Each 1 mm-diameter capillary tube contained $3\times10^6$ cells in PBS. On the left is a conventional $^{1}H$ image, and on the right is a $^{19}F$ image. The capillary tubes are embedded in agarose. Both images were acquired using a standard 2DFT spin-echo pulse sequence in an 11.7 T MRI system. The $^{1}H$ image was acquired with 256×256 image points, ~25 μm in-plane resolution, and 1 mm slice thickness, and the $^{19}F$ was acquired with 64×64 points, 100 μm in-plane resolution, and a 1 mm-thick slice.

To confirm that the PFPE-labeled immune cells are useful for MRI, in vitro $^{19}$F imaging of DC suspensions was performed. FSDCs were labeled in the same manner as described above. A phantom was prepared by embedding two 1 mm-diameter glass capillary tubes in agarose, where each capillary tube contained $3\times10^6$ DCs in phosphate buffered saline (PBS). One of the capillary tubes contained unlabeled cells (control). The phantom was placed on a laboratory-built RF surface coil that could be tuned to either $^1$H or $^{19}$F while in the magnet bore. Images were acquired using a standard 2DFT spin-echo pulse sequence in an 11.7 T MRI system. FIG. 2 shows the imaging results, where the left panel is the $^1$H image and the right panel is the $^{19}$F image. The $^{19}$F image shows a single intense spot in the region containing the capillary tube with the labeled cells. No chemical-shift artifacts could be detected. The $^{19}$F image has no background $^1$H signal; demonstrating the high selectivity of the imaging technology.

3. In Vivo MRI of PFPE-Labeled Immune Cells

The PFPE-labeled cells can be visualized in living subjects using MRI under a variety of conditions. Labeled DCs were imaged following either a focal implantation directly into tissues or an intravenous injection. These data show that the sensitivity of the imaging technology is sufficient for use in vivo with a variety of cell delivery methods.

Figure 3:
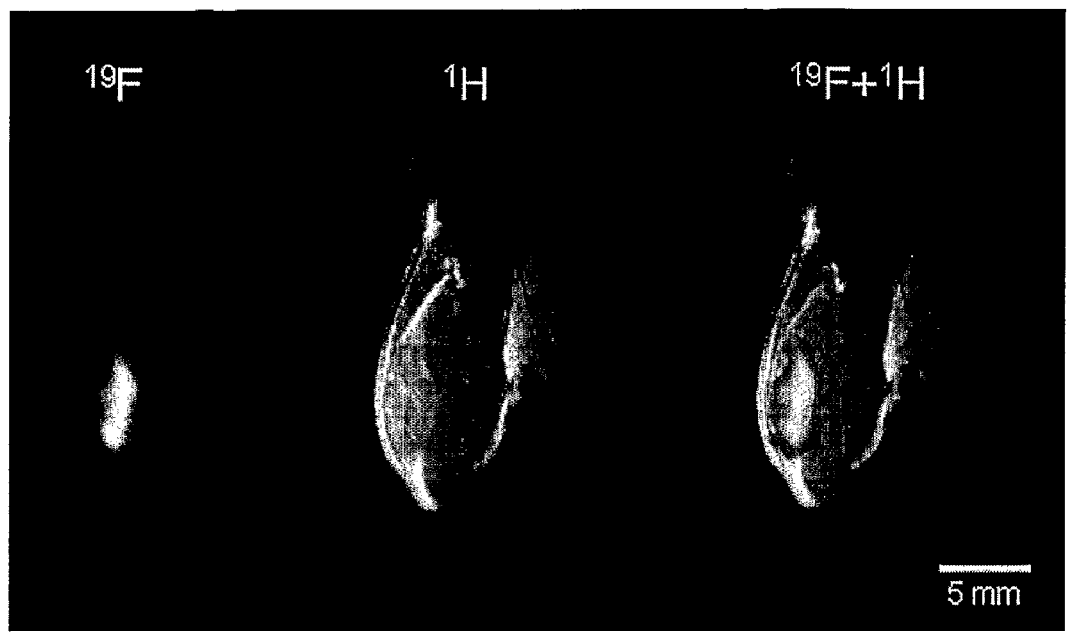
FIG. 3. In vivo MRI of mouse quadriceps after intramuscular injection of PFPE-labeled DCs. Shown (from left to right) are $^{19}F$ and $^{1}H$ coronal images and a composite $^{19}F+^{1}H$ image. The $^{19}$F image is displayed on a "hot-iron" intensity scale, and in the composite image (right) $^{19}$F is rendered semi-transparent. The $^1$H image was acquired with 256×256 image points, ~50 μm in-plane resolution, and a 1 mm slice thickness, and the $^{19}$F was acquired with 64×64 points, ~200 μm in-plane resolution, and a 1 mm-thick slice. The scale bar in the lower right corner is 5 mm. The mouse was anesthetized, intubated, and placed on a ventilator during the imaging session.

In one set of experiments $3\times10^6$ PFPE-labeled FSDCs in PBS were injected directly into the quadriceps muscle on one side of a mouse. The labeling methods were similar to those described above. Image data were acquired ~4 hours post-injection. The injected leg was positioned over a laboratory-built surface coil that could be tuned to either $^1$H or $^{19}$F. Images were acquired over a period of ~2 hours in an anesthetized mouse. Images for both nuclei were obtained using a standard 2DFT spin-echo pulse sequence on an 11.7 T MRI system. Typical results are shown in FIG. 3. Note that the $^{19}$F signal appears to track up from the site of injection. This movement may represent the migration of the DCs to the draining lymph node; it is known that a small proportion of DCs injected in this manner can be found in lymph nodes within hours. Also note that in the $^1$H image a small amount of hyperintensity is observed in the muscle in the same location as the labeled cells, which is consistent with the presence of resident inflammatory cells and the implanted DCs.

Figure 4:
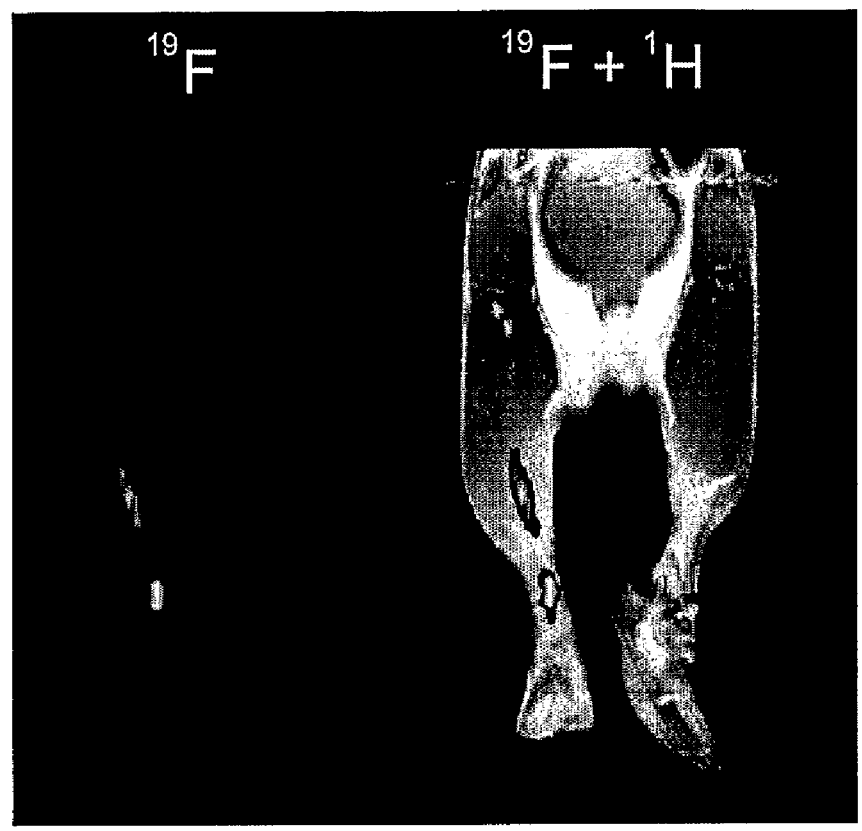
FIG. 4. In vivo MRI of DC migration into the mouse popliteal lymph node following hindfoot pad injection. PFPE-labeled DCs (3×10$^6$) were injected ~4 hours earlier. The left leg clearly shows an accumulation of labeled DCs in the ankle as well as a location consistent with the popliteal node. These coronal images were acquired and processed in a similar manner as described in FIG. 3. The $^1$H image was acquired with 256×256 image points, ~50 μm in-plane resolution, and 1.25 mm slice thickness. The $^{19}$F image was acquired with 128×64 points, ~200 μm in-plane resolution, and a 1.25 mm-thick slice.

FIG. 4 demonstrates the ability of the labeled PFPE-DCs to migrate to lymph nodes in vivo. In this experiment $3\times10^6$ labeled FSDCs were injected directly into the tip of the hind-foot pad. Images were acquired using similar parameters as FIG. 3. Approximately 4 hours later, an image of the injected leg shows that the cells have migrated and accumulated into the popliteal lymph node located adjacent to the knee (FIG. 4). The uninjected leg (right) shows no $^{19}$F signal.

Figure 5:
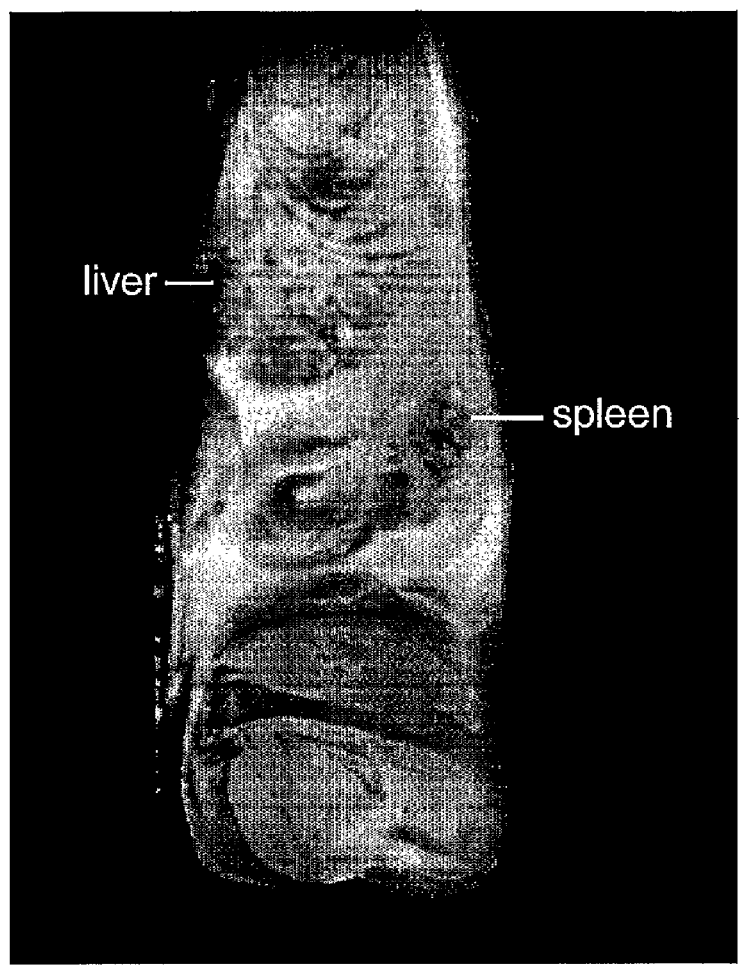
FIG. 5. In vivo oblique slice through the abdomen of a mouse that was inoculated with PFPE-labeled DCs. The $^{19}$F image is shown in hot-iron pseudo-color scale and is overlaid onto a grayscale anatomical $^1$H image. Cells are apparent in the liver, spleen, and possibly the lungs. This image was acquired approximately 4 hours after 10×10$^6$ labeled DCs were injected via the tail vein. Images were acquired using similar methods and parameters as described in FIG. 4.

In other studies, the feasibility of imaging PFPE-labeled DCs systemically following an intravenous injection was investigated. The mouse torso was imaged in vivo, and regions containing a concentrated accumulation of labeled cells were visualized. In these experiments, ~10×10$^6$ labeled FSDCs were labeled using the same method as above and were injected via the tail vein. Representative data is shown in FIG. 5. In this oblique slice through the torso the $^{19}$F signal is most apparent in the liver, spleen, and possibly the lungs (FIG. 5).

4. Phenotype Studies of PFPE-Labeled DCs

Figure 6:
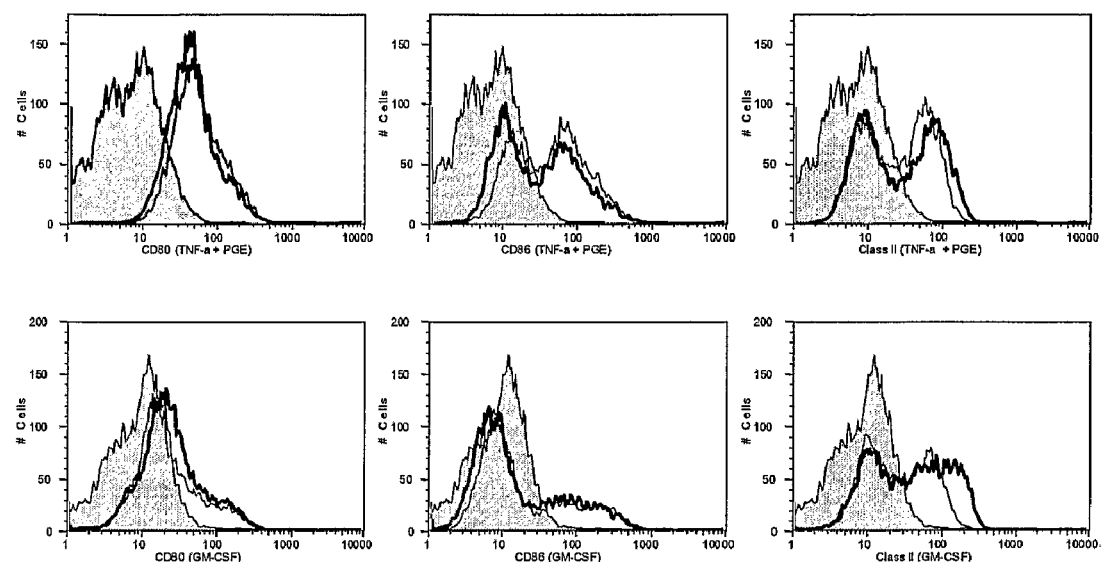
FIG. 6. Phenotypic FACS analysis of PFPE labeled (thick line) and unlabeled (thin line) bone marrow (BM) derived DCs. BM cells were gown in GM for 4 days and were either matured in the presence of TNF-α+PGE$_2$ (upper panels) or not (lower panels). Cells were stained with CD11c-PE (DC marker) and the indicated FITC-conjugated Abs. Results represent histograms of cells gated for CD11c expression. The shaded histograms represent the controls.

Applicants have performed several experiments to determine whether labeling of DCs with PFPE alters the cellular phenotype. Fluorescence activated cell sorting (FACS) experiments have been performed on primary BMDC cultures and in the FSDC line. Primary DCs were harvested from bone marrow cells extracted from NOD mice. BM cells were cultured in the presence of GM-CSF for 4 days as previously described [1]. On the fourth day maturation conditions were added to some of the cells, consisting of TNFα+PGE$_2$, and the remaining cells were cultured with GM-CSF alone. DCs cultured in only GM-CSF have an immature phenotype characterized by low levels of costimulatory molecule expression, whereas TNF-α and PGE$_2$ increases the expression of these molecules as well as the production levels of IL-12p70 cytokine. Cells were labeled with PFPE as described above. DCs were purified by magnetic cell sorting using anti-CD11c-coated magnetic microbeads. The phenotype of the cells was determined by flow cytometric analysis for the expression of DC and maturation-specific markers. The ability of the cells to secrete IL-12 was determined by incubating the DCs with CD40L-transfected J558 cells for 48 hours. When the cells were labeled with PFPE compounds there were no observed changes in the phenotype (FIG. 6). Similar results were also observed obtained for the DC line (data not shown).

5. Electron Microscopy of PFPE-Labeled DCs

Figure 7:
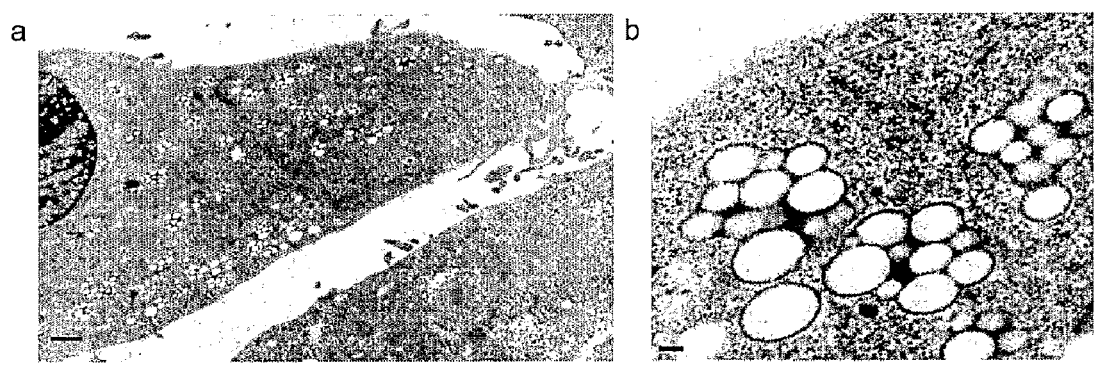
FIG. 7. Electron micrograph of PFPE-labeled DC. Shown is a representative labeled DC at low magnification (a) and at higher magnification (b). In (a), numerous light spots (PFPE particles) are observed inside the cell that are not observed in unlabeled cells (data not shown). In (b), particles appear as smooth spheroids. The perimeter of the particle is stained by the osmium. The particle diameters are ~100-200 nm. The scale bars represent 1 μm in (a) and 50 nm in (b).

To elucidate the intracellular distribution of PFPE emulsion particles, we performed electron microscopy (EM) on labeled cells. FIG. 7 shows typical results in a single cell. The emulsion particles are readily apparent in large numbers (FIG. 7a) and appear as smooth spheroids. The particles appear to be compartmentalized in regions that are consistent with phagocytic vacuoles (FIG. 7b). The osmium staining used to highlight intracellular structures also tends to delineate the boundaries of the PFPE particles (FIG. 7b).

FSDCs were labeled with PFPE emulsion particles as described above. The DCs were then washed, pelleted, and fixed in PBS containing 2% glutaraldehyde at room temperature for 30 minutes and held overnight at 4° C. The cells were washed three times in PBS and treated with 1% OSO$_4$ in PBS for 10 minutes. All of the samples were washed three times in H$_2$O and dehydrated in an ascending series of ethanol. Propylene oxide (PO) was used as a transitional solvent. The cells were infiltrated overnight in a solution containing a 1:1 mixture of PO and Epon-Araldite (EA). The next day the mixture was replaced with 100% EA, and the sample was placed in a desiccator for 8 hours. The sample was placed in plastic capsules containing EA and polymerized at 60 C.° for 48 hours. Thin (0.1 μm) sections were cut using a microtome and were placed on 200 mesh Cu grids. The samples were stained with 1% aqueous uranyl acetate and Reynolds lead citrate. Sections were imaged using a Hitach±7100 transmission electron microscope.

6. Intracellular Retention Time of PFPE Emulsions

Figure 8:
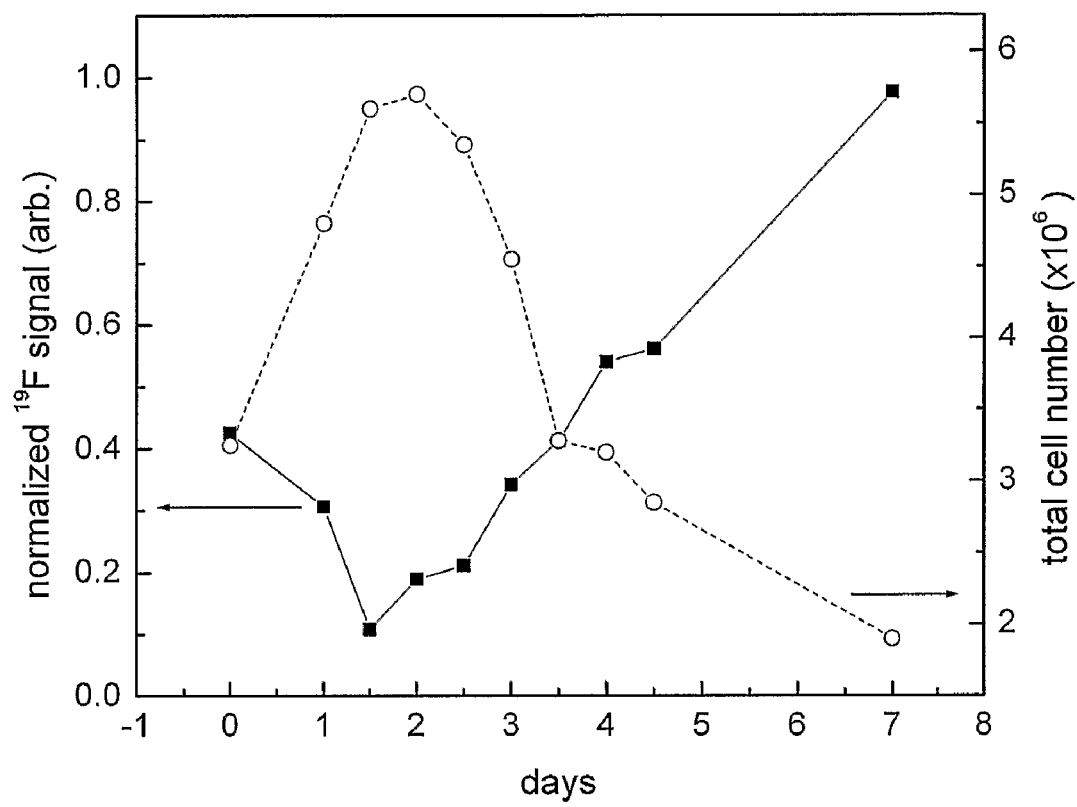
FIG. 8. The effective intracellular PFPE concentration (solid squares) and total cell number (open circles) as a function of time after DC labeling. The retention of the PFPE particles persists for many days in vitro. At each time-point a single tissue culture well was harvested and 1×10$^6$ cells were counted; these were then pelleted and assayed with $^{19}$F NMR. The left axis shows the integrated area under the $^{19}$F NMR peak normalized to a reference compound (trifluoroacetic acid) measured at the same time; the normalized signal is directly related to PFPE concentration. The right axis shows the total cell number in the plate. Note that at 2 days the cells in the plate become confluent and then there is a net cell loss at later times. Concurrently, the $^{19}$F signal initially decreases as expected due to dilution as a result of cell division; after the cells become overgrown and begin to die the remaining cells take up any excess PFPE in the media and the net $^{19}$F per cell increases.

Experiments were performed to estimate the intracellular retention time of the PFPE particles in vitro in FSDCs. The results show that there is little or no tendency for the cells to degrade or excrete the PFPE over time. At the experimental onset, numerous identical tissues culture dishes were plated with FSDCs and all were labeled with PFPE as described above. Following labeling, excess PFPE agents in the media were removed by thorough washing. The cells were then incubated at physiological conditions for one week. At various times over the course of a week, DCs in a single culture dish were washed of any PFPE released into the media. The cells were then harvested, pelleted, and the remaining intracellular PFPE concentration was assayed by acquiring $^{19}$F NMR spectra of the pellets (as described in Section 1). FIG. 8 shows the time-course for the PFPE retention over a period of a week. During the initial ~2 days cell division occurred at the normal rapid rate; this indicates that the PFPE did not effect cell division nor is it toxic. After the initial period of ~2 days the cells became confluent on the plates and some cell loss occurred as expected. Consequently, the $^{19}$F signal appears to increase in the remaining DCs due to the re-uptake of the PFPE particles that were released by the lysed apoptotic cells.

7. Boosting PFPE Labeling Efficiency Using Cationic Lipids

Figure 9:
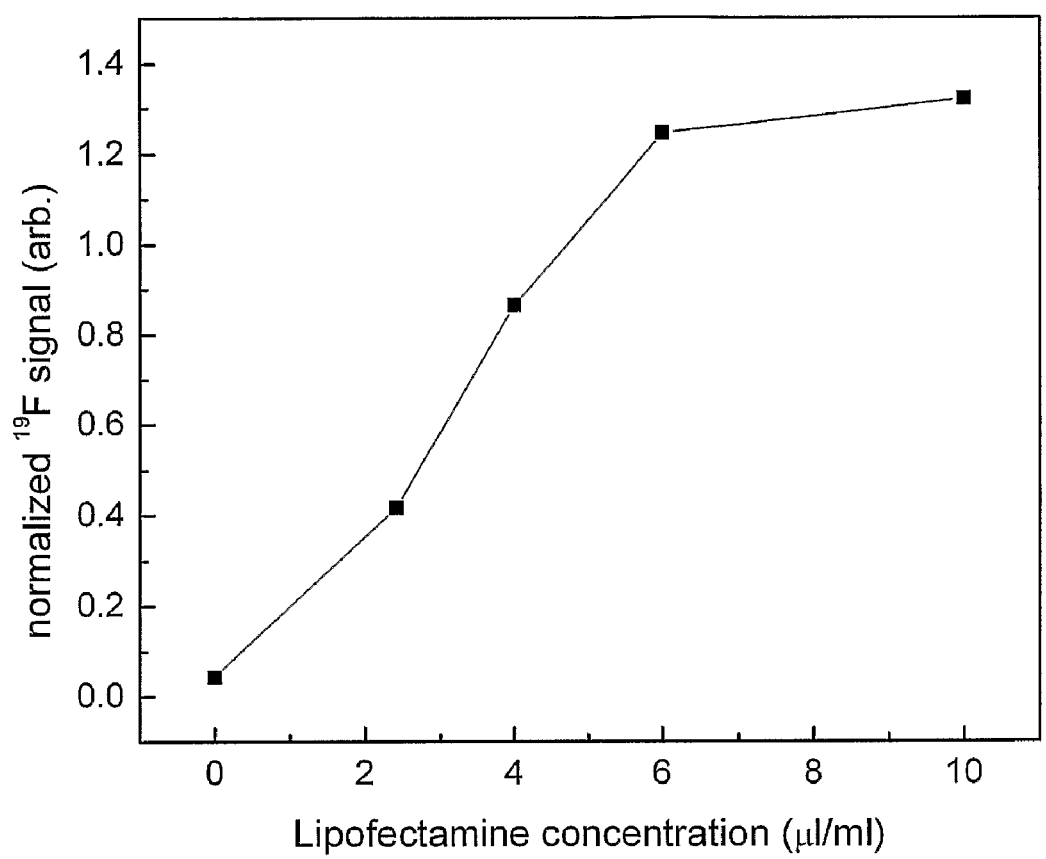
FIG. 9. PFPE concentration in DCs measured by $^{19}$F NMR as a function of Lipofectamine added. The maximum increase in PFPE uptake is observed to be 26-fold. All data was acquired after the same (4 hour) incubation period.

The experiments in this section demonstrate that the incorporation of cationic lipids into the surfactant for generating PFPE emulsions increases the intracellular uptake (FIG. 9). For each data point in FIG. 9, 1×10$^6$ FSDCs were labeled with PFPE as described in Section 1. Various amounts of cationic lipids (Lipofectamine™, Invitrogen Inc.) were pre-mixed with the PFPE emulsion before it was added to the media. After the incubation period, cells were thoroughly washed of excess PFPE, pelleted, and the PFPE content was assayed from the normalized $^{19}$F NMR signal as described above. The results show that a dramatic increase in cellular uptake can be achieved for a range of Lipofectamine concentrations (FIG. 9). Approximately a 26-fold increase in uptake is observed at the highest levels of Lipofectamine studied (FIG. 9). EM results in fixed cells confirmed that the PFPE particles were intracellular.

8. PFPE Cytotoxicity and Effects on Cell Proliferation

Figure 10:
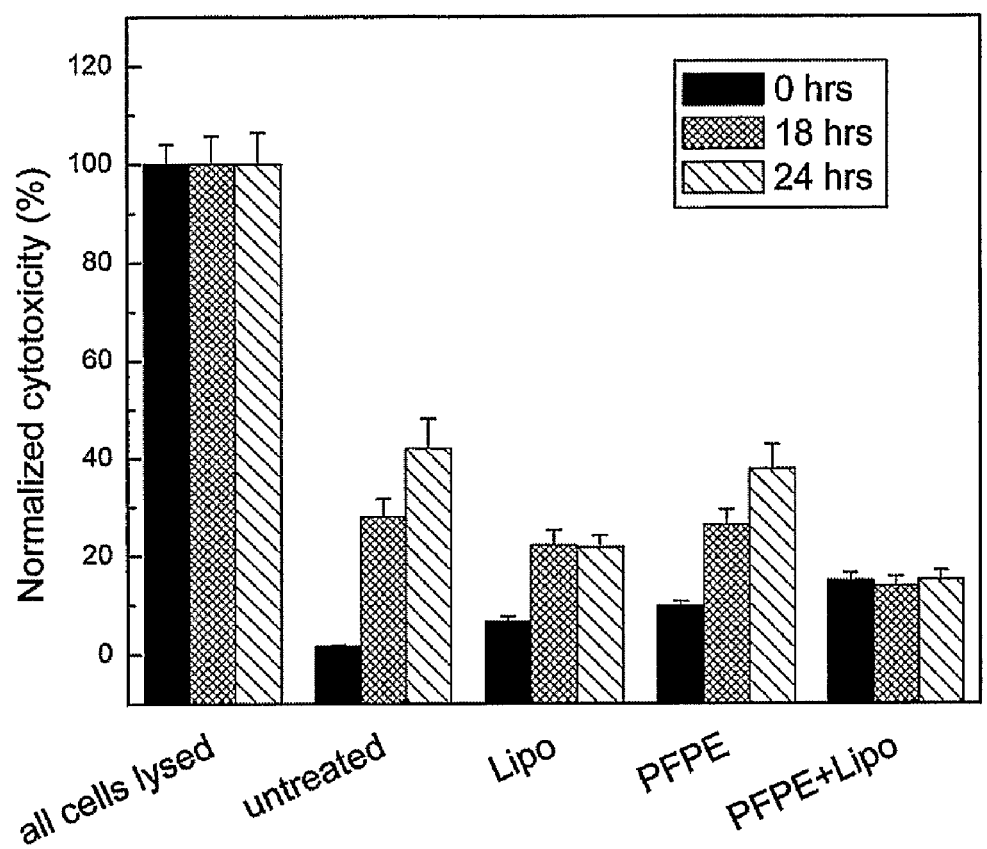
FIG. 10. Cytotoxicity of PFPE-labeled DCs measured by G6PD enzyme release. Shown are cells at 0, 18, and 24 hours post-labeling and controls. The incubation conditions (left to right) are all cells lysed (i.e. mimicking 100% toxicity), nothing added (untreated), Lipofectamine added (Lipo), PFPE added (PFPE), and PFPE+Lipofectamine added (PFPE+Lipo). Values are given as the mean±SEM (standard error of the mean) for N=8.

PFPE has essentially no toxic effects on cells after uptake. Following PFPE-labeling the fraction of cells surviving was determined using the Vybrant Cytotoxicity Assay (Molecular Probes, Eugene, Oreg.). This assay measures the leakage of a specific enzyme (glucose 6-phosphate dehydrogenase, G6PD) from the cytoplasm into the surrounding culture media, and it is a widely accepted method to estimate the number of non-viable cells in a population. G6PD reduces the NAD+ provided in the reaction mix to NADH, which in turn favors the reduction of the non-fluorescent resazurin into the fluorescent resorufin. Within an hour the cytotoxicity in as few as 500 cells can be measured using a microplate reader. Applicants incubated the FSDCs for 3 hours at 37° C. with PFPE, PFPE plus Lipofectamine transfection agent (to boost intracellular uptake), Lipofectamine alone, and plain cells. The cells were then washed, counted, and seeded into 96-well microplates. At times 0, 18, and 24 after labeling the cells were assayed according to the manufacturer's directions. FIG. 10 shows the results. Overall, there is little or no apparent toxicity for all times studied.

Figure 11:
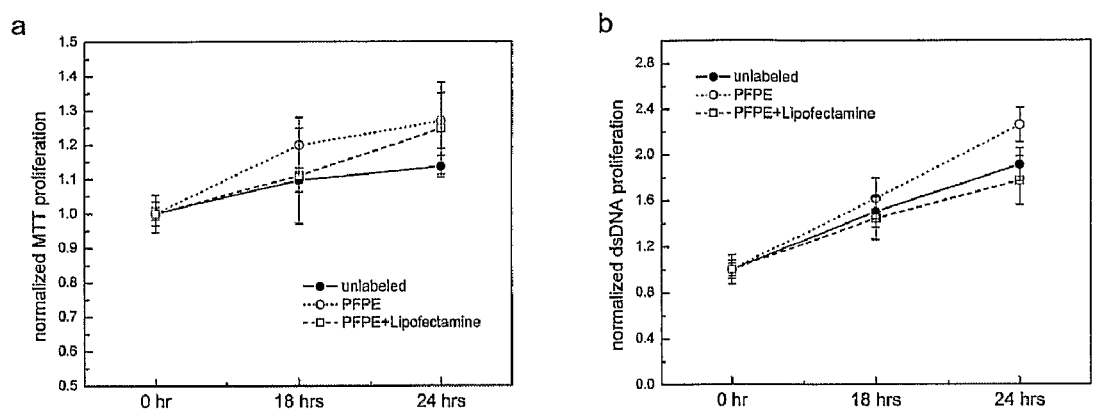
FIG. 11. Proliferation of PFPE-labeled DCs assayed by MTT (a) and dsDNA (b). Cells were incubated for 3 hours at 37° C. with (left to right) nothing added (unlabeled), Lipofectamine added (Lipo), PFPE added (PFPE), PFPE+Lipofectamine added (PFPE+Lipo). Values are given as the mean±SEM (standard error of the mean) for N=16.

To test whether PFPE-labeling had any adverse effect on cellular proliferation, applicants have used two complementary methods, including the MTT and the total double stranded DNA (dsDNA) assays. The mitochondrial, or MTT assay (ATCC, Manassas, Va.), provides information about the cells' response to external factors. The yellow methyl thiazole tetrazolium (MTT) is reduced to purple formazan by dehydrogenases in the intact mitochondria. After cell lysis the formazan's absorbance is photometrically quantified in a 96-well microplate reader. The PFPE-labeled cells and controls were prepared identically to those described for the G6PD cytotoxicity assay (above). Following the manufacturer's instructions, the MTT proliferation was assayed at 0, 18, and 24 hours post-labeling. FIG. 11a shows the normalized MTT absorption versus time. No significant difference among the groups is observed.

The total cell number over time can also be accurately measured by fluorescent techniques. Applicants have used the FluoReporter Blue Fluorometric dsDNA Quantification Kit (Molecular Probes, Eugene, Oreg.) which contains a cell-permeant dye (Hoechst 33258). Upon binding nonintercalatively to A/T-rich regions of dsDNA, the fluorescence yield of bis-benzimidazole increases linearly with the number of cells in the sample. Labeled FSDCs and controls were prepared in an identical fashion as for the MTT and G6PD cytotoxicity assays. Cells were assayed at 0, 18, and 24 hours post-labeling according to the manufacturer's instructions using a microplate reader. The results are shown in FIG. 11b. Little or no significant difference in cell proliferation was observed between labeled cells and unlabeled cells.

9. Linear PFPE Imaging Reagents

Figure 12:
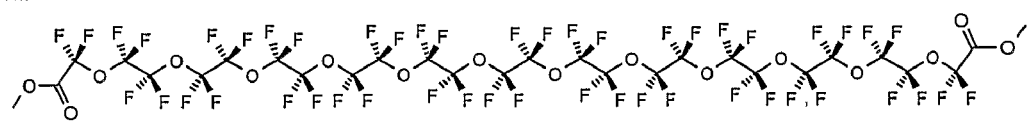
FIG. 12. Molecular structure of linear PFPE ester (a) and $^{19}$F NMR spectrum of the emulsions made from this molecule (b). The linear PFPE (a) has an average of 48 F atoms. The NMR shows one main peak at −92 ppm from the internal $CF_2$-groups and two much smaller peaks from the end groups. The unemulsified bulk PFPE compound has an identical NMR spectrum (data not shown). The $^{19}$F NMR data were acquired at 282 MHz.
Figure 12:
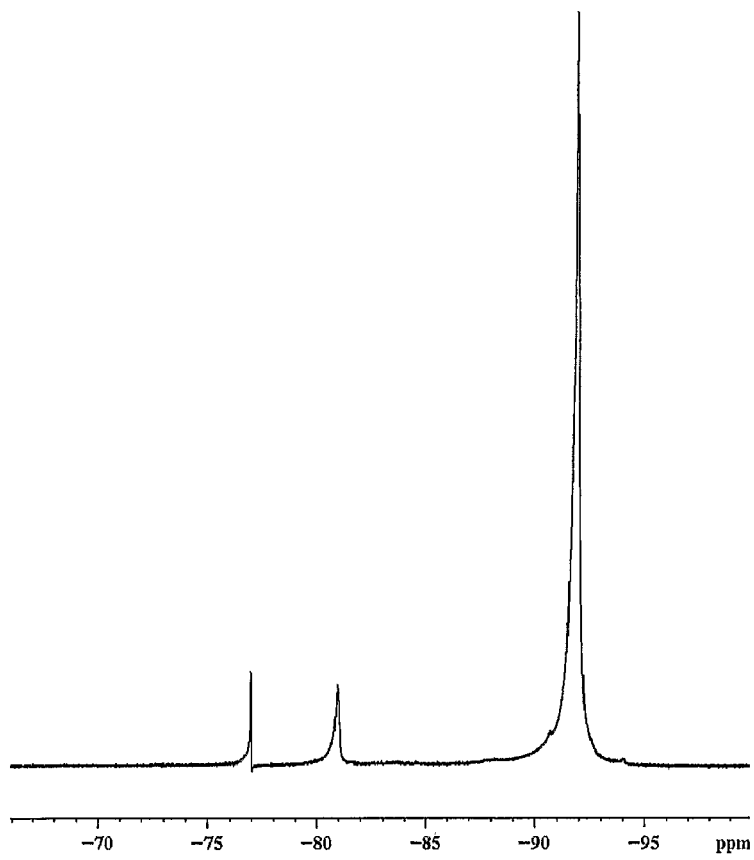
Figure 13:
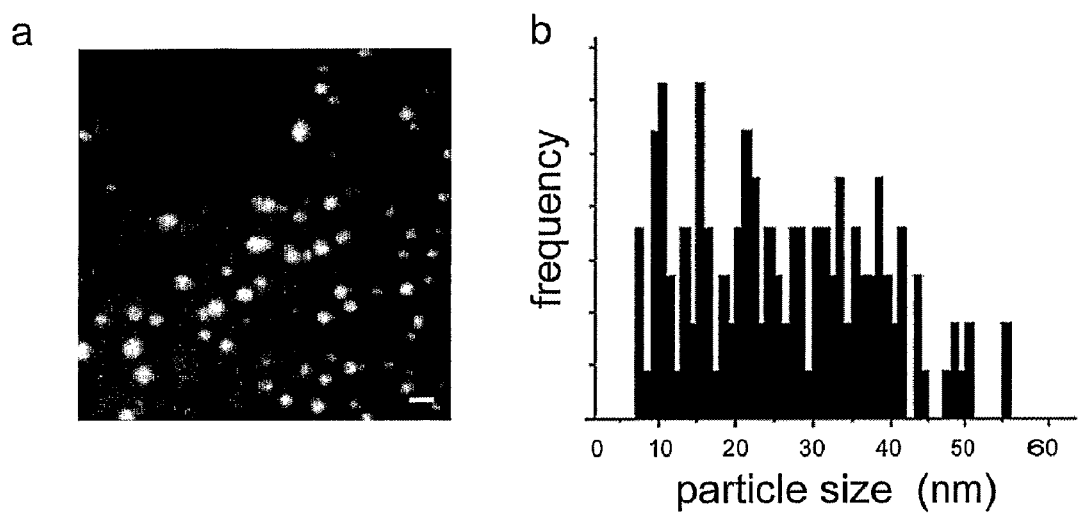
FIG. 13. Electron microscopy of linear PFPE emulsion particles (a) and histogram of particle sizes (b). From (b), the mean particle size is 42±19 nm (N=133). The emulsions were prepared by spraying onto carbon-coated grids, air dried and imaged. The scale bar=100 nm.

A 1,600 MW linear polyethylene oxide terminated with methyl ester functional groups was synthesized according to the methods described in U.S. Pat. Nos. 5,539,059. Applicants have successfully synthesized emulsions from the linear PFPE ester (FIG. 12a). Thus far, the final product has been characterized by $^{19}$F NMR (FIG. 12b) and EM (FIG. 13a). This material gives one major $^{19}$F NMR resonance with a small side peak that is acceptable for MRI applications. If needed, off-resonance saturating RF pulses may be used to eliminate image ghosts from the small peak. The EM data was used to assay emulsion particle size. FIG. 13b shows a histogram of particle sizes calculated from multiple EM micrographs. Sizes were calculated in an automated fashion using a commercial software program (Scion Corp., Fredrick, Md.). The mean particle size was calculated to be 42±19 nm (error is standard deviation). This particle size is smaller than the perfluoro-15-crown-5 ether emulsions used for the results shown above, and the smaller size is well suited to the imaging technology. To make these emulsions, dimethyl ester PFPE was heated with polyethylene glycol (PEG) 600 MW and O-(2-Aminoethyl)-O-methyl polyethylene glycol 750 (Sigma-Aldrich) at 85° C. for 48 hrs. A 2:1 mole ratio of PEG:PFPE was used. Methylene chloride and lecithin (from egg phospholipids, Sigma, St. Louis, Miss.) were added to the mixture and desiccated in pure nitrogen. Distilled H$_2$O was added, and the mixture was sonicated for 3 min to form emulsions.

Figure 14:
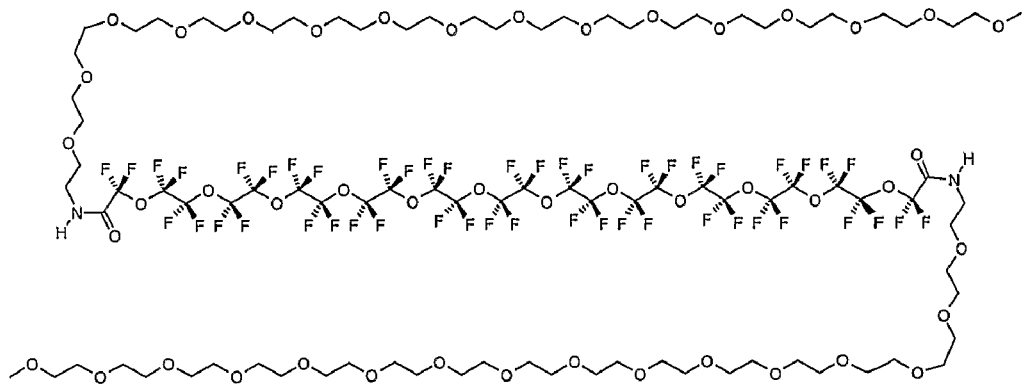
FIG. 14. Illustrations of a linear PFPE imaging reagent and example reactions for generating derivatives.
Figure 14:
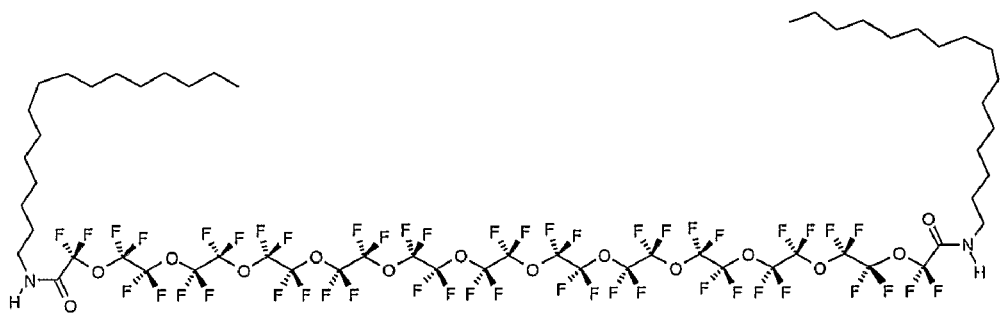
Figure 14:
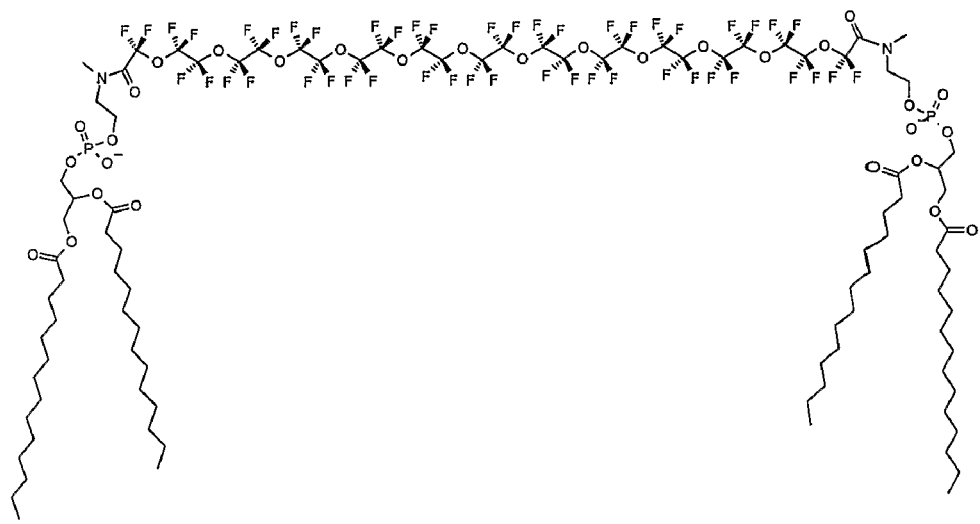
Figure 14:
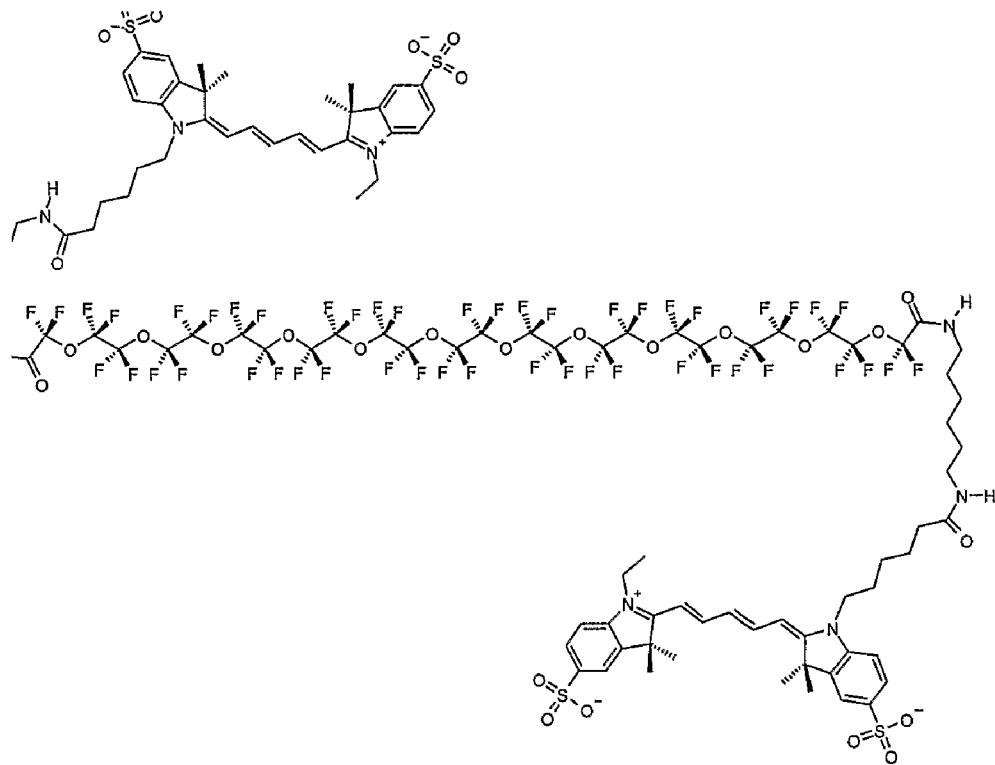

The linear PFPE ester reacts readily to produce derivatives with a range of properties. The reaction chemistry of the end groups of polyethylene glycols is well understood and may be exploited to prepare a range of conjugated imaging reagents. As outlined in FIG. 14, hydrophilic and lipophilic moieties may be attached to this PFPE forming water-soluble and lipid-soluble conjugates, respectively. Coupling polyethylene glycol (PEG) groups to this PFPE will make a tri-block copolymer with water-soluble regions on each end and a hydrophobic region in the center (FIG. 14, Rxn 1). The properties of the tri-block copolymers are adjusted by varying the size of the PEG sections relative to the PPO section. Block copolymers containing water-soluble, fluorocarbon, and hydrocarbon sections are known to segregate into domains with each polymer type associating only with itself [46]. The PEG-PFPE-PEG copolymer is expected to behave similarly, forming micelles with a PFPE core surrounded by a water-soluble PEG coat. Amino-PEG blocks are commercially available with a range of molecular weights. Coupling the PFPE core with other groups, such as aliphatic amines (FIG. 14, Rxn 2 and 4a) and phosphatidyl ethanolamine (FIG. 14, Rxn 3) in place of the PEG sections, will give derivatives with different solubility characteristics. Dual-mode agents composed of PFPE with fluorescent dye endgroups, such as Cy5 (FIG. 14, Rxn 4b), may be prepared. As is the case for fluorescently tagged proteins, the fluorescent dyes can act as markers for the distribution and localization of the conjugates within cells and can be used with FACS analysis and optical microscopy.

As prepared previously, the perfluoro-15-crown-5 ether may be emulsified in a mixture of 2% lecithin and 2% safflower oil using sonication, forming average droplets of ~100-200 nm. Many other surfactant compositions (e.g. Pluronics) know to those skilled in the art can be used in the formation of similar emulsions. Micelles of the linear PFPE derivatives may also be formed by sonication. Emulsification of perfluoropolyethers has been described by Visca, et al. [44] and Brunetta [43]. These procedures will be used as a basis for producing emulsions of PFPE derivatives. The high water solubility of CyDyes will produce micelles similar to the PEG-PFPE couples. Additional surfactants, such as lecithin, may be added as needed to produce small, stable micelles. Formation of micelles may be optimized for maximum PFPE content.

The final PFPE content of the emulsions and micelles may be measured by using $^{19}$F NMR relative to a known concentration of trifluoroacetic acid. The average particle size of each emulsion may be estimated by EM or light scattering techniques. EM micrographs or light scattering may also be used to calculate histograms of particle diameters.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

1. Feili-Hariri, M., et al., *Immunotherapy of NOD mice with bone marrow-derived dendritic cells*. Diabetes, 1999. 48: p. 2300-2308.
2. Pluchino, S., et al., *Injection of adult neurospheres induces recovery in a chronic model of multiple sclerosis*. Nature, 2003. 422(6933): p. 688-694.
3. Yeh, T. C., et al., *In-vivo dynamic MRI tracking of rat T-cells labeled with superparamagnetic iron-oxide particles*. Magn Reson Med, 1995. 33: p. 200-208.
4. Schulze, E., et al., *Cellular uptake and trafficking of a prototypical magnetic iron oxide label in vitro*. Invest Radiol, 1995. 30(10): p. 604-10.
5. Moore, A., R. Weissleder, and A. Bogdanov, *Uptake of dextran-coated monocrystalline iron oxides in tumor cells and macrophages*. JMRI-Journal of Magnetic Resonance Imaging, 1997. 7(6): p. 1140-1145.
6. Weissleder, R., et al., *Magnetically labeled cells can be detected by MR imaging*. JMRI-Journal of Magnetic Resonance Imaging, 1997. 7(1): p. 258-263.
7. Schoepf, U., et al., *Intracellular magnetic labeling of lymphocytes for in vivo trafficking studies*. Biotechniques, 1998. 24(4): p. 642-+.

8. Ye, Q., et al., *In vivo detection of acute rat renal allograft rejection by MRI with USPIO particles*. Kidney International, 2002. 61(3): p. 1124-1135.
9. Dousset, V., et al., *In vivo macrophage activity imaging in the central nervous system detected by magnetic resonance*. Magnetic Resonance in Medicine, 1999. 41(2): p. 329-333.
10. Josephson, L., et al., *High-efficiency intracellular magnetic labeling with novel superparamagnetic-tat peptide conjugates*. Bioconjugate Chemistry, 1999. 10(2): p. 186-191.
11. Dodd, C. H., et al., *Normal T-cell response and in vivo magnetic resonance imaging of T cells loaded with HIV transactivator-peptide-derived superparamagnetic nanoparticles*. Journal of Immunological Methods, 2001. 256 (1-2): p. 89-105.
12. Ahrens, E. T., et al., *Receptor-mediated endocytosis of iron-oxide particles provides efficient labeling of dendritic cells for in vivo MR imaging*. Magn. Reson. Med., 2003. 46(6): p. 1006-1013.
13. Hoehn, M., et al., *Monitoring of implanted stem cell migration in vivo: A highly resolved in vivo magnetic resonance imaging investigation of experimental stroke in rat*. Proceedings of the National Academy of Sciences of the United States of America, 2002. 99(25): p. 16267-16272.
14. Lewin, M., et al., *Tat peptide-derivatized magnetic nanoparticles allow in vivo tracking and recovery of progenitor cells*. Nature Biotechnology, 2000. 18(4): p. 410-414.
15. Kanno, S., et al., *Macrophage accumulation associated with rat cardiac allograft rejection detected by magnetic resonance imaging with ultrasmall superparamagnetic iron oxide particles*. Circulation, 2001. 104(8): p. 934-938.
16. Fishman, J. E., et al., *Oxygen-sensitive 19F NMR imaging of the vascular system in vivo*. Magn Reson Imaging, 1987. 5(4): p. 279-85.
17. Eidelberg, D., et al., *19F NMR imaging of blood oxygenation in the brain*. Magn Reson Med, 1988. 6(3): p. 344-52.
18. Dardzinski, B. J. and C. H. Sotak, *Rapid tissue oxygen tension mapping using 19F inversion-recovery echo-planar imaging of perfluoro-15-crown-5-ether*. Magn Reson Med, 1994. 32(1): p. 88-97.
19. Noth, U., et al., *In-vivo measurement of partial oxygen-pressure in large vessels and in the reticuloendothelial system using fast 19F-MRI*. Magn Reson Med, 1995. 34(5): p. 738-745.
20. Lutz, J., et al., *Measurement of oxygen tensions in the abdominal cavity and in the skeletal muscle using 19F-MRI of neat PFC droplets*. Oxygen Transport to Tissue Xix, 1997. 428: p. 569-572.
21. Duong, T. Q. and S. G. Kim, *In vivo MR measurements of regional arterial and venous blood volume fractions in intact rat brain*. Magn. Reson. Med., 2000. 43(3): p. 393-402.
22. McGoron, A. J., et al., *Perfluorocarbon distribution to liver, lung and spleen of emulsions of perfluorotributylamine (FTBA) in pigs and rats and perfluorooctyl bromide (PFOB) in rats and dogs by F-19 NMR-spectroscopy*. Artificial Cells Blood Substitutes and Immobilization Biotechnology, 1994. 22(4): p. 1243-1250.
23. Noth, U., et al., *Perfluoro-15-crown-5-ether labelled macrophages in adoptive transfer experimental allergic encephalomyelitis*. Artificial Cells Blood Substitutes and Immobilization Biotechnology, 1997. 25(3): p. 243-254.
24. Girolomoni, G., et al., *Establishment of a cell-line with features of early dendritic cell precursors from fetal mouse skin*. European Journal of Immunology, 1995. 25(8): p. 2163-2169.

EQUIVALENTS

While specific embodiments of the subject inventions are explicitly disclosed herein, the above specification is illustrative and not restrictive. Many variations of the inventions will become apparent to those skilled in the art upon review of this specification and the claims below. The full scope of the inventions should be determined by reference to the claims, along with their full scope of equivalents, and the specification, along with such variations.

The invention claimed is:
1. A method for detecting a cell in a subject comprising:
  a. administering to the subject a cell that is labeled with a fluorocarbon imaging reagent, wherein at least a portion of the fluorocarbon imaging reagent is internalized into the cell; and
  b. examining at least a portion of the subject by $^{19}$F magnetic resonance imaging, thereby detecting the cell that is labeled with the fluorocarbon imaging reagent in the subject.
2. An ex vivo labeled cellular formulation comprising:
  a. a cell; and
  b. a fluorocarbon imaging reagent that is detectable by $^{19}$F magnetic resonance imaging and that is associated with the cell.
3. A method for detecting transplanted cells in a transplant recipient comprising:
  a. administering cells for transplant to a transplant recipient, at least a portion of which cells for transplant are labeled with a fluorocarbon imaging reagent, wherein at least a portion of the fluorocarbon imaging reagent is internalized into the cell;
  b. examining at least a portion of the subject by $^{19}$F magnetic resonance imaging, thereby detecting the cells that are labeled with the fluorocarbon imaging reagent in the subject.
4. The method of claim 1, further comprising contacting the cell ex vivo with a fluorocarbon imaging reagent under conditions such that the fluorocarbon imaging reagent becomes associated with the cell prior to step a.
5. The method of claim 1, wherein the fluorocarbon imaging reagent is a perfluoropolyether.
6. The method of claim 1, wherein the cell is contacted with the fluorocarbon imaging reagent in the presence of an uptake enhancing reagent.
7. The method of claim 6, wherein the uptake enhancing reagent comprises a cationic lipid.
8. The method of claim 1, wherein at least a portion of the fluorocarbon imaging reagent is associated with the extracellular surface of the cell.
9. The method of claim 1, wherein the fluorocarbon imaging reagent is conjugated to a cellular targeting moiety.
10. The method of claim 9, wherein the cellular targeting moiety comprises an antibody that binds to an epitope that is exposed to the extracellular milieu.
11. The method of claim 1, wherein the fluorocarbon imaging reagent is conjugated to an internalization moiety.
12. The method of claim 1, wherein the cell is a mammalian cell.
13. The method of claim 1, wherein the cell is a cell of the immune system.
14. The method of claim 1, wherein the cell is a dendritic cell.
15. The method of claim 1, wherein the fluorocarbon imaging reagent is formulated as an emulsion.

16. The method of claim 1, wherein the emulsion comprises particles having a mean diameter of between 30 and 500 nm.

17. The method of claim 1, wherein the fluorocarbon imaging reagent is a perfluoro-crown ether.

18. The method of claim 17, wherein the imaging reagent is a perfluoro-15-crown-5-ether.

19. The method of claim 1, wherein the fluorocarbon is a perfluorinated polyether having an average formula:

XO(Y—O)$_n$Z wherein Y is selected from the group consisting of:

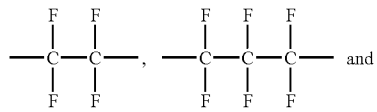 and

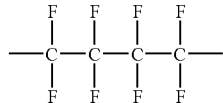

wherein n is an integer from 8 to 20; wherein X and Z are the same and are selected from the group consisting of perfluoroalkyls, perfluoroethers, fluoroalkyls terminated with fluoroacyl, carboxyl, amide or ester, methylols, acid chlorides, amides, amidines, acrylates and esters.

20. The method of claim 1, wherein the imaging reagent comprises an additional functional moiety.

21. The method of claim 20, wherein the additional functional moiety is a detection moiety.

22. The method of claim 21, wherein the detection moiety is selected from the group consisting of: a fluorescent detection moiety and a PET detection moiety.

* * * * *